US011419750B2

(12) United States Patent
Brown

(10) Patent No.: US 11,419,750 B2
(45) Date of Patent: *Aug. 23, 2022

(54) CUSTOM-FIT DENTAL GUARD

(71) Applicant: Brown Innovation, LLC, Lake Quivira, KS (US)

(72) Inventor: Thomas W. Brown, Lake Quivira, KS (US)

(73) Assignee: Brown Innovation, LLC, Lake Quivira, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/993,999

(22) Filed: May 31, 2018

(65) Prior Publication Data

US 2018/0344510 A1   Dec. 6, 2018

Related U.S. Application Data

(60) Provisional application No. 62/514,381, filed on Jun. 2, 2017.

(51) Int. Cl.
| | | |
|---|---|---|
| *B29C 45/14* | (2006.01) | |
| *B29C 45/16* | (2006.01) | |
| *A61F 5/56* | (2006.01) | |
| *B29L 31/00* | (2006.01) | |

(52) U.S. Cl.
CPC ........ *A61F 5/566* (2013.01); *A61F 2005/563* (2013.01); *B29C 45/14* (2013.01); *B29C 45/16* (2013.01); *B29L 2031/753* (2013.01)

(58) Field of Classification Search
CPC ...... A61F 5/56; A61F 2005/563; A61F 5/566; A63B 71/085; A63B 2071/086; A63B 2071/088; A61C 7/143; A61C 7/36; A61C 7/06; A61C 7/08; A61C 7/10; A61C 7/12; A61C 7/14; A61C 7/141; A61C 7/80
See application file for complete search history.

(56) References Cited

U.S. PATENT DOCUMENTS

| | | | |
|---|---|---|---|
| 3,496,936 A * | 2/1970 | Gores ................. | A63B 71/085 128/861 |
| 4,664,109 A * | 5/1987 | Rasocha ................. | A62B 9/06 128/201.11 |
| 5,339,832 A | 8/1994 | Kittelsen et al. | |
| 5,386,821 A | 2/1995 | Poterack | |
| (Continued) | | | |

OTHER PUBLICATIONS

Perstop, CapaTM 6500 Product Data Sheet, Apr. 23, 2009. (Year: 2009).*

(Continued)

*Primary Examiner* — Niki Bakhtiari
*Assistant Examiner* — Nicholas J Chidiac
(74) *Attorney, Agent, or Firm* — Hovey Williams LLP

(57) ABSTRACT

A dental guard (10) for preventing wear of the occlusal surfaces of a user's teeth resulting from bruxism is provided. The dental guard (10) can be can be custom-fitted to the teeth of the wearer. The guard (10) comprises a durable core (14) that is overmolded by a thermoplastic outer layer (12). The outer layer (12) can be softened through exposure to hot, but not boiling, water, and then formed around the user's teeth. The guard (10) may include one or more features (32, 84) that assist the user in proper positioning of the guard within his or her mouth during the custom fitting process.

17 Claims, 22 Drawing Sheets

(56) References Cited

U.S. PATENT DOCUMENTS

| | | | |
|---|---|---|---|
| 5,865,619 A * | 2/1999 | Cross, III | A61F 5/566 433/6 |
| 6,082,363 A | 7/2000 | Washburn | |
| 7,481,224 B2 * | 1/2009 | Nelson | A61F 2/00 128/848 |
| 7,954,496 B2 | 6/2011 | Jansheski et al. | |
| 7,971,591 B2 * | 7/2011 | Jansheski | A61C 7/08 128/848 |
| 8,678,010 B2 | 3/2014 | Wright | |
| 9,022,903 B2 * | 5/2015 | Rafih | A63B 71/085 482/121 |
| 2004/0154626 A1 | 8/2004 | Washburn | A63B 71/085 128/861 |
| 2006/0084024 A1 * | 4/2006 | Farrell | A61C 7/08 433/6 |
| 2007/0048347 A1 | 3/2007 | Bardach et al. | |
| 2007/0254256 A1 * | 11/2007 | Farrell | A63B 71/085 433/6 |
| 2007/0270631 A1 * | 11/2007 | Nelson | A61F 2/00 600/12 |
| 2007/0270632 A1 * | 11/2007 | Nelson | A61F 2/00 600/12 |
| 2008/0138766 A1 * | 6/2008 | Jansheski | A61C 7/08 433/140 |
| 2009/0165805 A1 * | 7/2009 | Syrop | A61F 5/566 128/861 |
| 2011/0067711 A1 * | 3/2011 | Jansheski | A61F 5/566 128/861 |
| 2012/0231932 A1 * | 9/2012 | Rafih | A63B 71/085 482/11 |
| 2012/0260924 A1 | 10/2012 | Foster | |
| 2014/0238418 A1 * | 8/2014 | Turkbas | A61C 19/063 128/862 |
| 2017/0281324 A1 | 10/2017 | Cheetham | |
| 2018/0014912 A1 * | 1/2018 | Radmand | A61C 8/0016 |

OTHER PUBLICATIONS

Office Action in corresponding U.S. Appl. No. 15/993,953, dated Jul. 7, 2020.
Ethylene Vinyl Acetate, Copolymer Safety Data Sheet, International Polymers Company (2020).
LSR 2050 Liquid Silicon Rubber, General Purpose, 2020 Matweb.
Office Action in corresponding U.S. Appl. No. 15/994,023, dated Aug. 7, 2020.
Office Action in corresponding U.S. Appl. No. 15/993,984, dated Nov. 10, 2020.
Office Action in corresponding U.S. Appl. No. 15/993,953, dated Jan. 26, 2021.
Office Action in corresponding U.S. Appl. No. 15/994,023, dated May 12, 2021.
Office Action in corresponding U.S. Appl. No. 15/993,953, dated May 25, 2021.

* cited by examiner

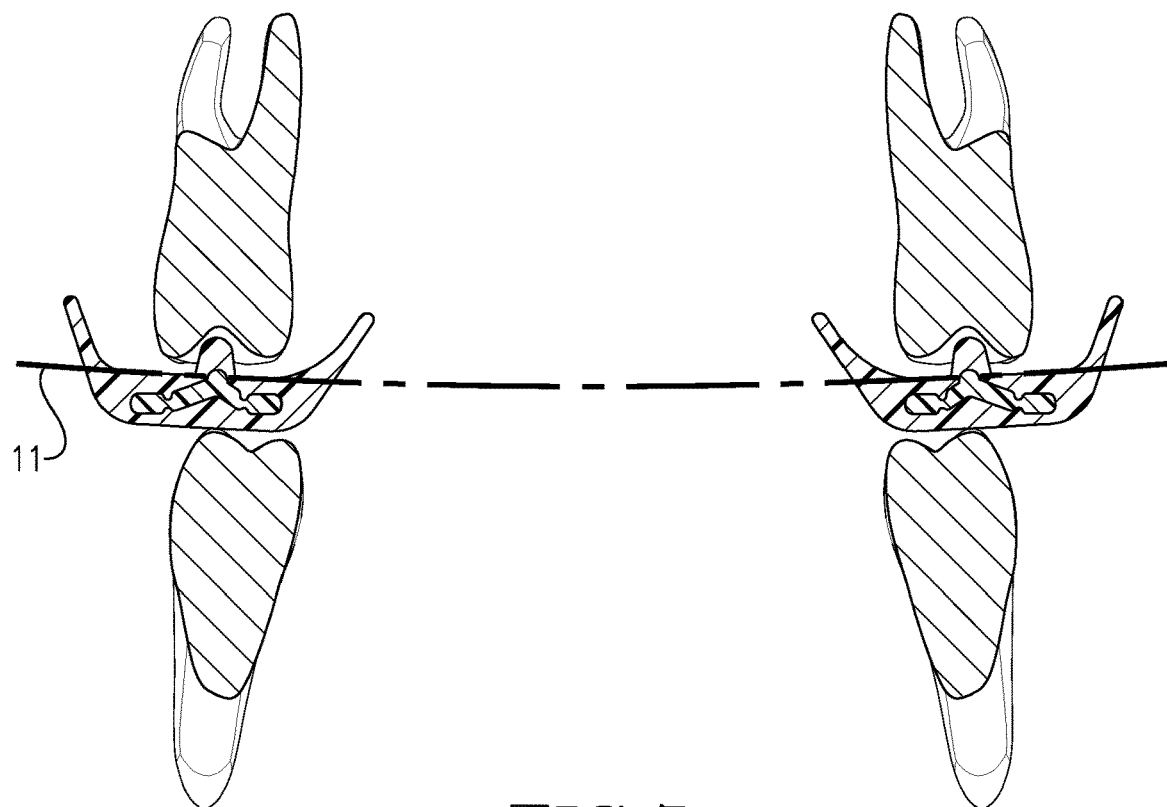
FIG. 7a
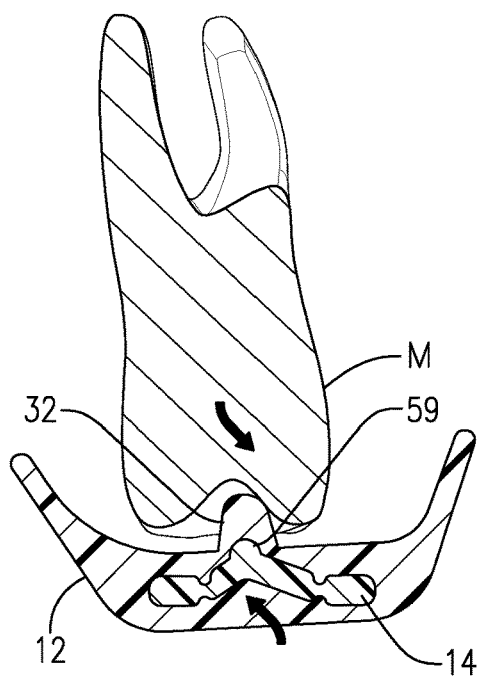 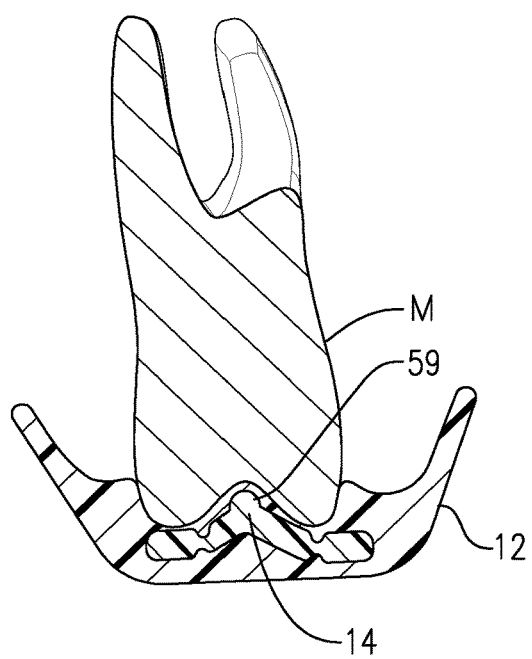
FIG. 7b  FIG. 7c

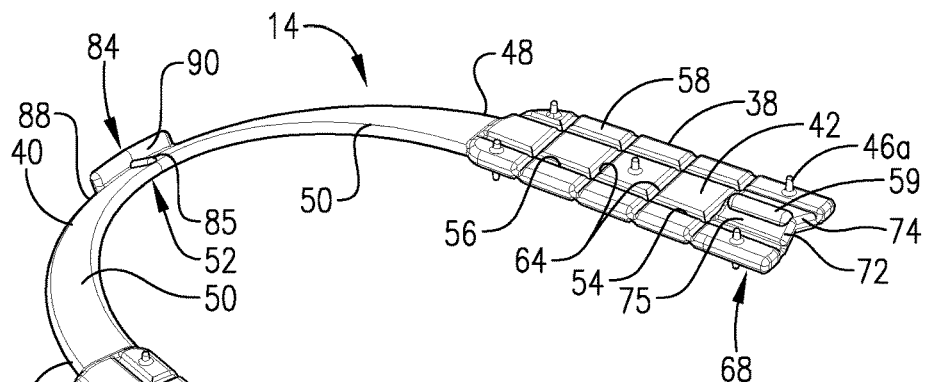
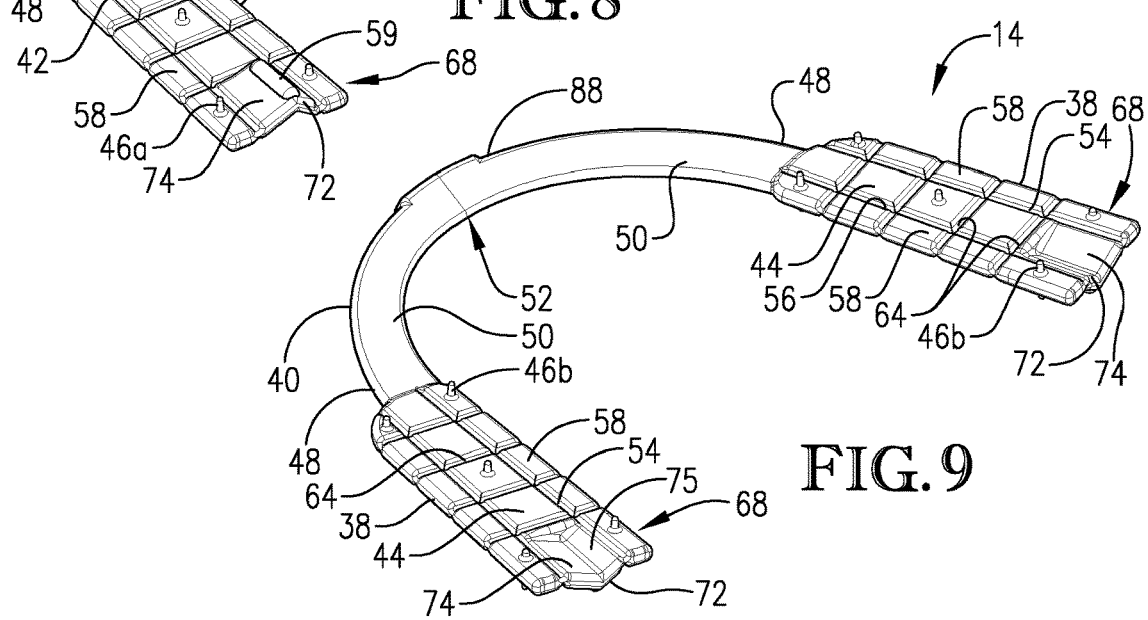
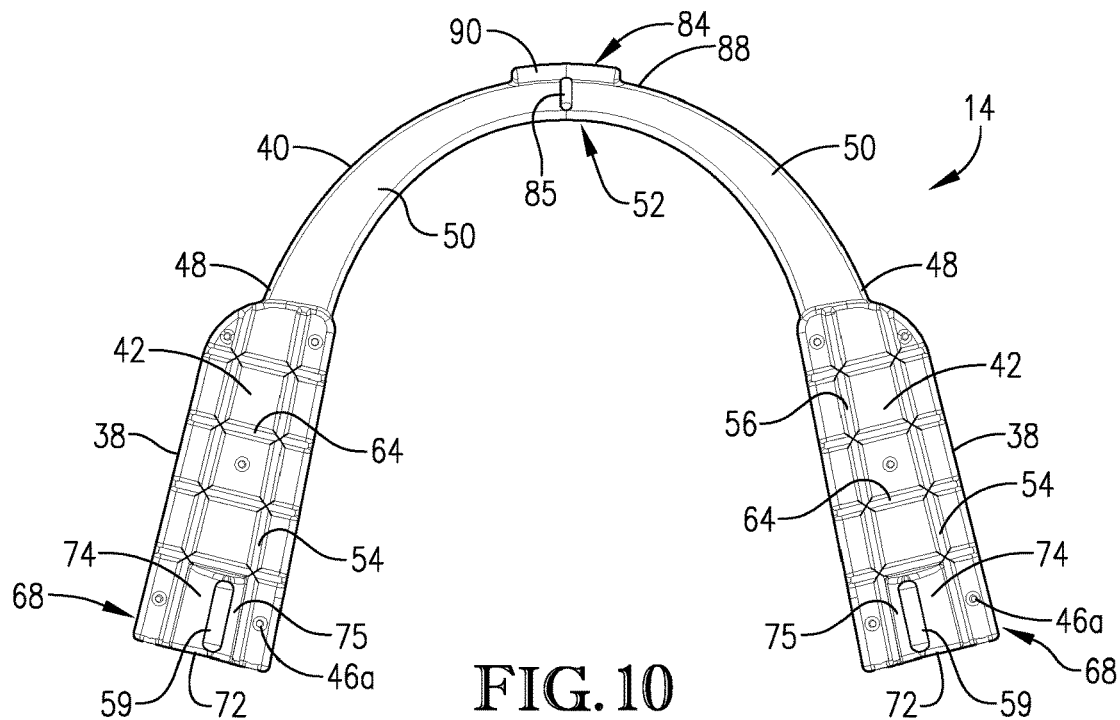

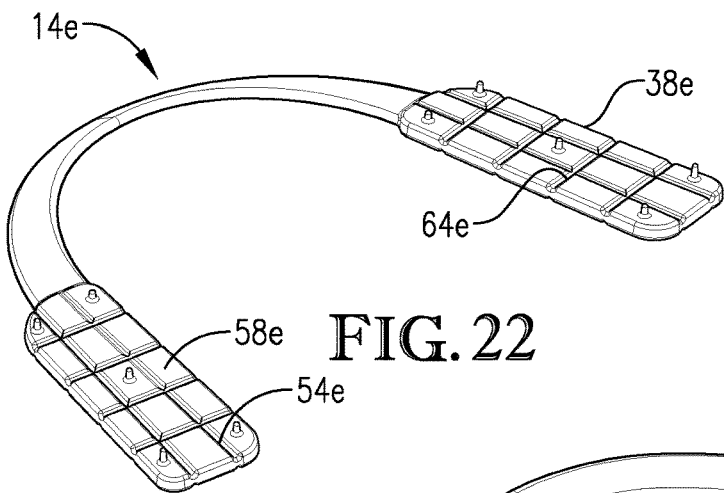
FIG. 22
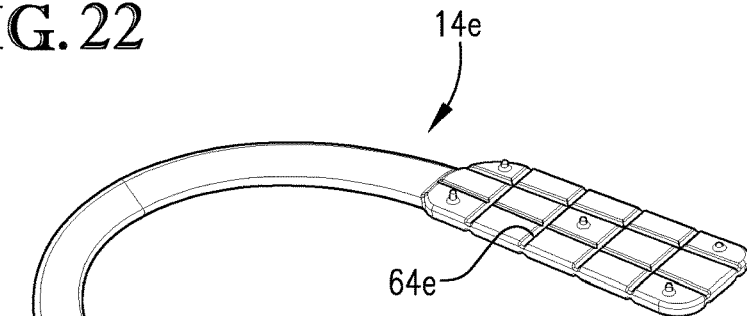
FIG. 23
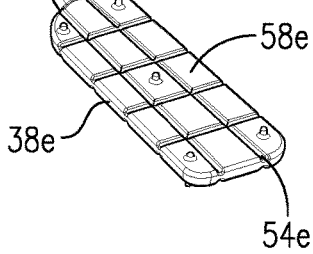
FIG. 24
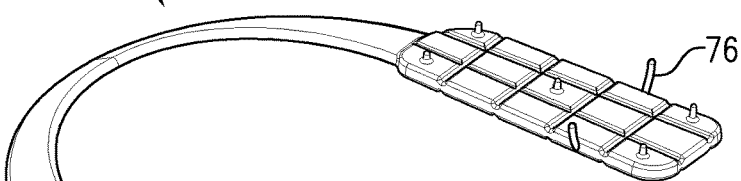
FIG. 25

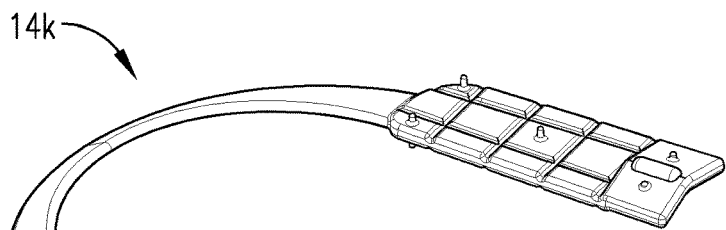
FIG. 34
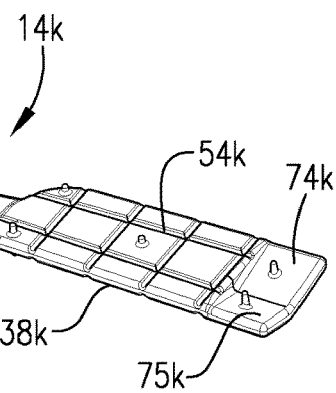
FIG. 35
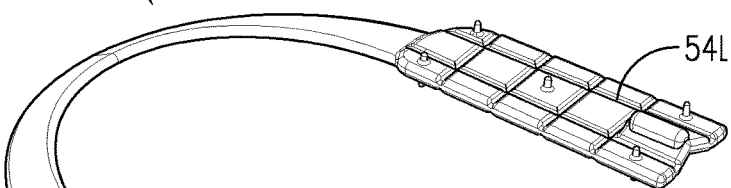
FIG. 36
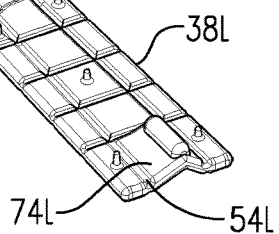
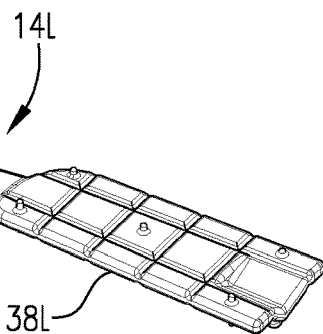
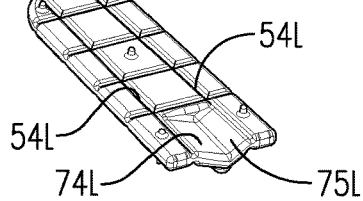
FIG. 37

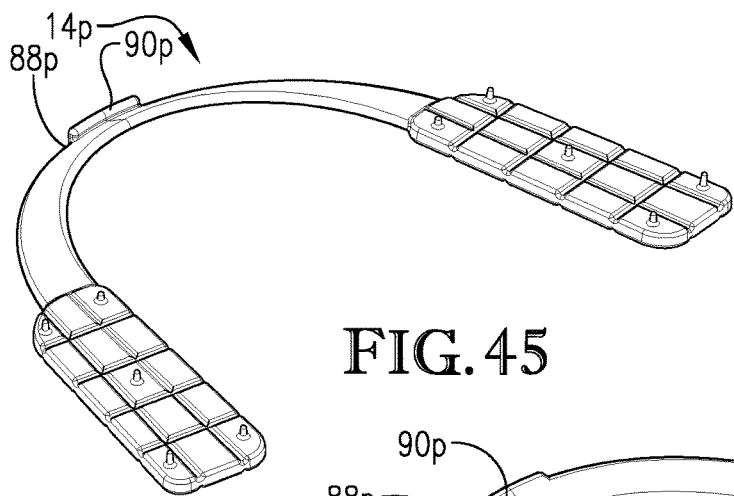
FIG. 45
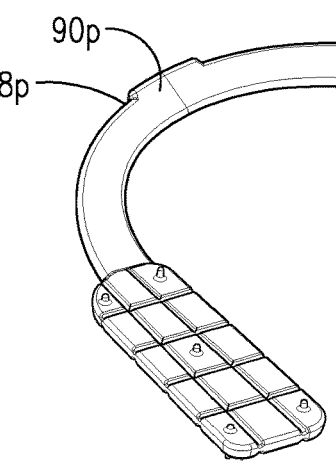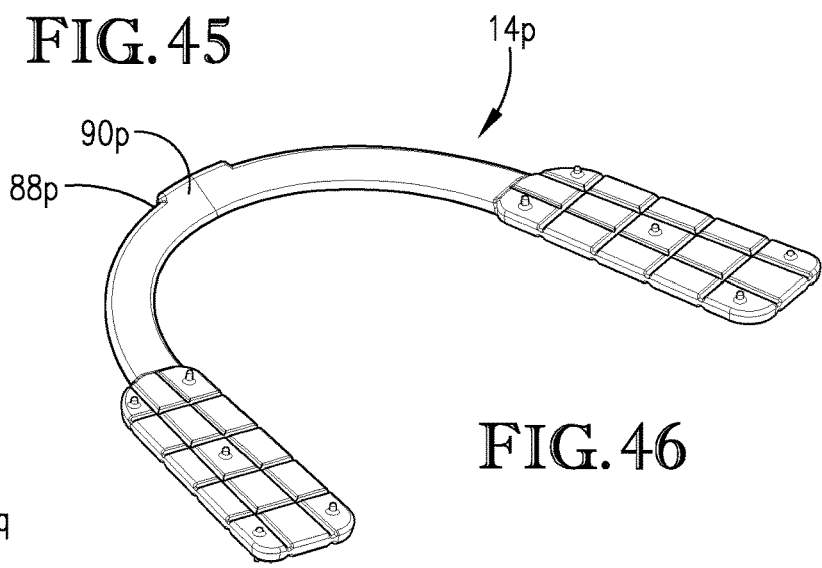
FIG. 46
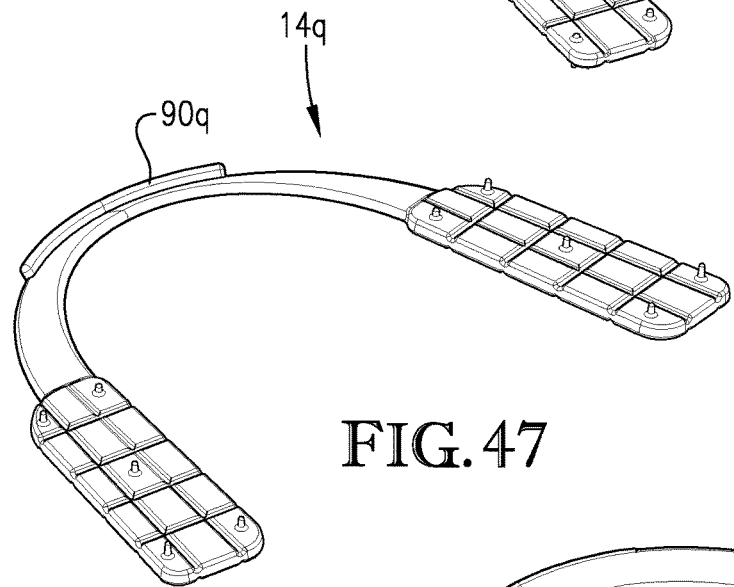
FIG. 47
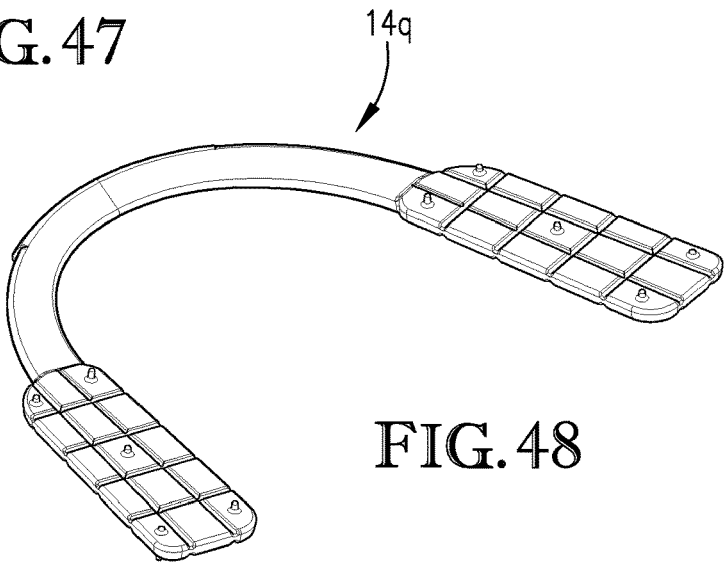
FIG. 48

CUSTOM-FIT DENTAL GUARD

RELATED APPLICATION

This application claims the benefit of U.S. Provisional Patent Application No. 62/514,381, filed Jun. 2, 2017, which in incorporated by reference herein in its entirety.

BACKGROUND OF THE INVENTION

Field of the Invention

The present invention is generally directed toward an interocclusal device for preventing the ill effects of bruxism. In particular, the dental guard can be custom-fitted to the teeth of the wearer by first softening the guard through exposure, for example, to hot, but not boiling, water. In certain embodiments, the dental guard comprises a core that is overmolded by a thermoplastic material that has a much lower softening point temperature than the core. The core reinforces the occlusal surfaces of the guard to prevent the user's teeth from penetrating through the guard during custom-fitting and usage of the guard.

Description of the Prior Art

Bruxism is a common problem afflicting a large portion of the general population, most of whom are unaware of the condition, which can manifest itself during sleep. Uncontrolled or unmitigated clenching and grinding of the teeth can result in symptoms such as abnormal tooth wear, tooth fractures, pain or tenderness of the temporomandibular joints, and teeth hypersensitivity. The adverse effects of bruxism can be mitigated by wearing an appliance that prevents the occlusal surfaces of the user's maxillary and mandibular teeth from making contact. Instead, of enamel-to-enamel contact, the user's teeth contact the appliance material, which tends to be much softer. Thus, tooth wear can be prevented, even if the user continues to clench and grind during sleep.

A number of dental guards have been proposed to deal with the effects of bruxism. For example, U.S. Pat. No. 8,316,859 describes an interocclusal appliance that comprises a two-piece preform including a base material and an impression material. However, with this appliance, the impression material is moldable only to the maxillary teeth, for example, and not to the occlusal surfaces of mandibular teeth. Moreover, the appliance can have a fairly significant profile when inserted into the user's mouth leading to an uncomfortable separation between the maxillary and mandibular teeth.

U.S. Pat. No. 8,689,797 describes a customizable dental appliance, primarily geared for use by athletes. These mouth guards also tend to be quite bulky and are unamenable to being worn for extended periods, such as overnight.

U.S. Pat. No. 9,345,556 describes a nighttime dental guard that is formable by heating the guard in a microwave oven. However, the device must be placed into a water-filled case, which is then placed into the microwave oven and heated. The dental guard may be made from a propylene-based elastomer, which may lack extended durability that some users require.

Other exemplary dental guards include those disclosed in U.S. Pat. Nos. 9,403,079, 5,103,838, 8,733,364, 8,701,673, 8,196,587, 7,913,695, 7,832,404, D677,007, 6,820,623, 8,074,658, 6,691,710, 6,675,806, 6,626,180, 6,598,605, 6,588,430, 6,581,604, 6,539,943, 6,415,794, 6,257,239, 7,305,990, 7,299,804, 7,156,774, 7,047,978, 6,986,354, 6,935,857, 6,932,088, D504,744, 6,397,848, 6,302,110, 6,200,133, 6,164,278, 5,879,155, 5,865,619, 5,836,761, 5,732,715, 5,718,575, and 5,682,904. However, all of these guards present problems in that they are not fully customizable to the user's teeth, are bulky when inserted into the user's mouth, or lack extended durability due to materials used in their construction. Moreover, these dental guards generally do not provide adequate assistance to ensure proper positioning of the guard within the user's mouth, particularly during forming of the guard.

SUMMARY OF THE INVENTION

Embodiments of the present invention overcome at least one of these shortcomings of prior dental guards. According to one embodiment of the present invention there is provided a dental guard comprising a core formed from a first material having a first softening point temperature. The core comprises a pair of bite pads interconnected by an anterior arch segment. Each of the bite pads comprises opposed maxillary and mandibular occlusal surfaces. The guard further comprises an outer layer overmolded onto the core and substantially covering the maxillary and mandibular occlusal surfaces of the pair of bite pads. The outer layer is formed from a second material having a second softening point temperature that is less than the first softening point temperature. The outer layer defines, at least in part, a channel adapted to receive maxillary teeth of a user.

According to another embodiment of the present invention, there is provided a dental guard comprising a channel formed from a thermoplastic material having a softening temperature that is below the boiling point of water. The channel is adapted to receive maxillary teeth of a user. The guard further comprises at least one positioning element extending from a posterior surface of the channel and adapted to be received in the occlusal groove between the buccal and lingual cusps of a maxillary or mandibular molar.

According to yet another embodiment of the present invention, there is provided a method of using a dental guard as described herein. The method comprises heating the dental guard to a temperature less than the boiling point of water thereby softening at least a portion of the dental guard and positioning the dental guard within a user's mouth so that at least some of the user's maxillary teeth reside within and contact at least one surface of the channel.

According to still another embodiment of the present invention, there is provided a method of manufacturing a dental guard. The method comprises overmolding a core formed from a first material having a first softening point temperature with a second material having a second softening point temperature using an injection molding process. The core comprises a pair of bite pads interconnected by an anterior arch segment, each of the bite pads comprising opposed maxillary and mandibular occlusal surfaces. The second material forms an outer layer that substantially covers the maxillary and mandibular occlusal surfaces of the bite pads and defines, at least in part, a channel adapted to receive maxillary teeth of a user. The second softening point temperature is less than the first softening point temperature.

According to further embodiments the present invention, there are provided bite pad cores for use in the construction of dental guards according to the present invention. In one particular embodiment, the bite pad core comprises a pair of bite pads interconnected by an anterior arch segment. Each of the bite pads comprises opposed maxillary and mandibular occlusal surfaces. The bite pads comprise one or more flexible hinges formed therein that divide the bite pads into respective bite pad segments. The one or more hinges permit pivoting of at least one bite pad segment relative to another bite pad segment.

In another embodiment, the bite pad core comprises a pair of bite pads interconnected by an anterior arch segment. Each of the bite pads comprises opposed maxillary and mandibular occlusal surfaces. The maxillary occlusal surfaces of one of the bite pads are located within a first plane, and at least a portion of the arch segment has a maxilla-facing surface located within a second plane. The relative angle between the first plane and the second plane being from about 30° to about 60°.

In another embodiment, the bite pad core comprises a pair of bite pads interconnected by an anterior arch segment. Each of the bite pads comprises opposed maxillary and mandibular occlusal surfaces, and a positioning element located in a posterior portion of each bite pad and extending from the maxillary occlusal surface of each bite pad. The positioning element is adapted to be received in the occlusal groove between the buccal and lingual cusps of a maxillary molar.

BRIEF DESCRIPTION OF THE DRAWINGS

FIG. 7a is a posterior cross-sectional view of the dental guard of FIG. 1 illustrating the guard's positioning relative to the Curve of Wilson;

FIGS. 7b and 7c are cross-sectional views illustrating how the positioning elements interact with the user's molar in order to properly align the dental guard during custom fitting;

FIG. 8 is a top isometric view of the core utilized in the dental guard of FIG. 1;

FIG. 9 is a bottom isometric view the core utilized in the dental guard of FIG. 1;

FIG. 10 is a top plan view of the core utilized in the dental guard of FIG. 1;

FIG. 22 is a top isometric view of another embodiment of a core that may be utilized in the construction of a dental guard according to the present invention having a plurality of longitudinal and transverse hinges formed in each bite pad;

FIG. 23 is a bottom isometric view of the core of FIG. 22;

FIG. 24 is a top isometric view of another embodiment of a core that may be utilized in the construction of a dental guard according to the present invention having a pair of positioning elements extending from the side of each bite pad;

FIG. 25 is a bottom isometric view of the core of FIG. 24;

FIG. 34 is a top isometric view of another embodiment of a core that may be utilized in the construction of a dental guard according to the present invention having a raised positioning element extending from the maxillary occlusal surface of each bite pad, the posterior portion of the bite pad having sloped maxillary and mandibular occlusal surfaces;

FIG. 35 is a bottom isometric view of the core of FIG. 34;

FIG. 36 is a top isometric view of another embodiment of a core that may be utilized in the construction of a dental guard according to the present invention having a raised positioning element extending from a hinged posterior portion of each bite pad;

FIG. 37 is a bottom isometric view of the core of FIG. 36;

FIG. 45 is a top isometric view of another embodiment of a core that may be utilized in the construction of a dental guard according to the present invention having a more prominent anterior positioning element extending from the anterior arch segment and configured to engage the anterior surfaces of the user's central incisors;

FIG. 46 is a bottom isometric view of the core of FIG. 45;

FIG. 47 is a top isometric view of another embodiment of a core that may be utilized in the construction of a dental guard according to the present invention having an anterior positioning element extending from the anterior arch segment that extends along a greater length of the anterior arch segment;

FIG. 48 is a bottom isometric view of the core of FIG. 47;

DETAILED DESCRIPTION OF THE PREFERRED EMBODIMENT

Figure 1:
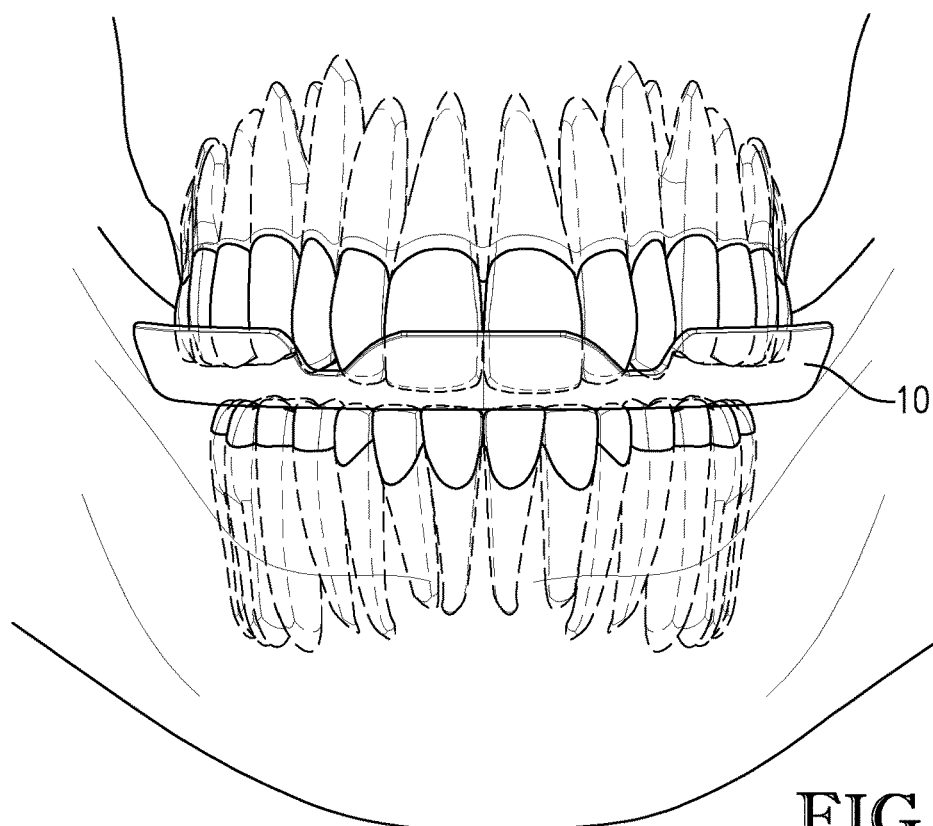
FIG. 1 is an anterior elevation view of a dental guard in accordance with the present invention placed within the mouth of a user.
Figure 2:
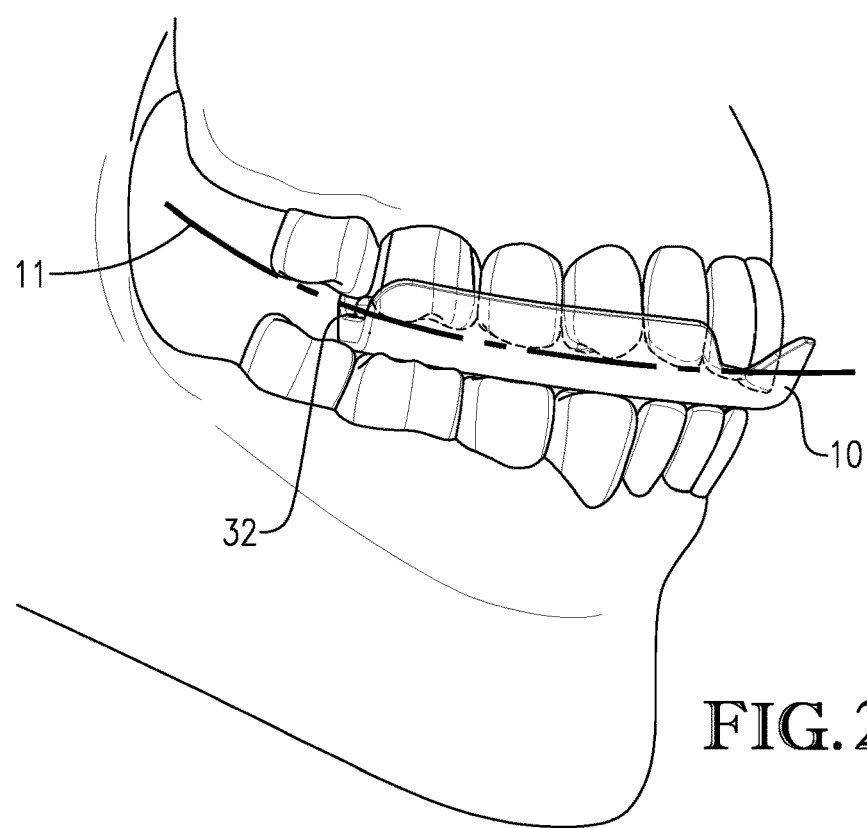
FIG. 2 is a buccal elevation view of the dental guard of FIG. 1 placed within the mouth of a user and illustrating the guard's positioning relative to the Curve of Spee.

FIGS. 1 and 2 illustrate a non-custom-fitted dental guard 10 in accordance with the present invention. As can be seen, guard 10 is nearly a full-mouth guard fitting over substantially all of the user's teeth except for a portion of the user's first molars. Thus, the guard 10 prevents contact between the user's maxillary and mandibular teeth, and especially the occlusal surfaces thereof, so as to prevent wear of the occlusal surfaces due to bruxism. While it is understood that no two individuals will be identical, the guard 10 is configured to conform to common structural dental characteristics of a typical user. In particular, FIG. 2 demonstrates that the guard 10 is configured to conform to the user's Curve of Spee 11 and Curve of Wilson 13 (see, FIG. 7) thereby maintaining a natural feel when worn by the user. As described in greater detail below, the guard is adapted to be custom-fitted to the user's teeth much in the same way a clinical dental guard would be fitted. However, the present guard 10 permits the end user to perform the custom fitting at home, rather than require that the guard is fabricated by a dental professional.

Figure 3:
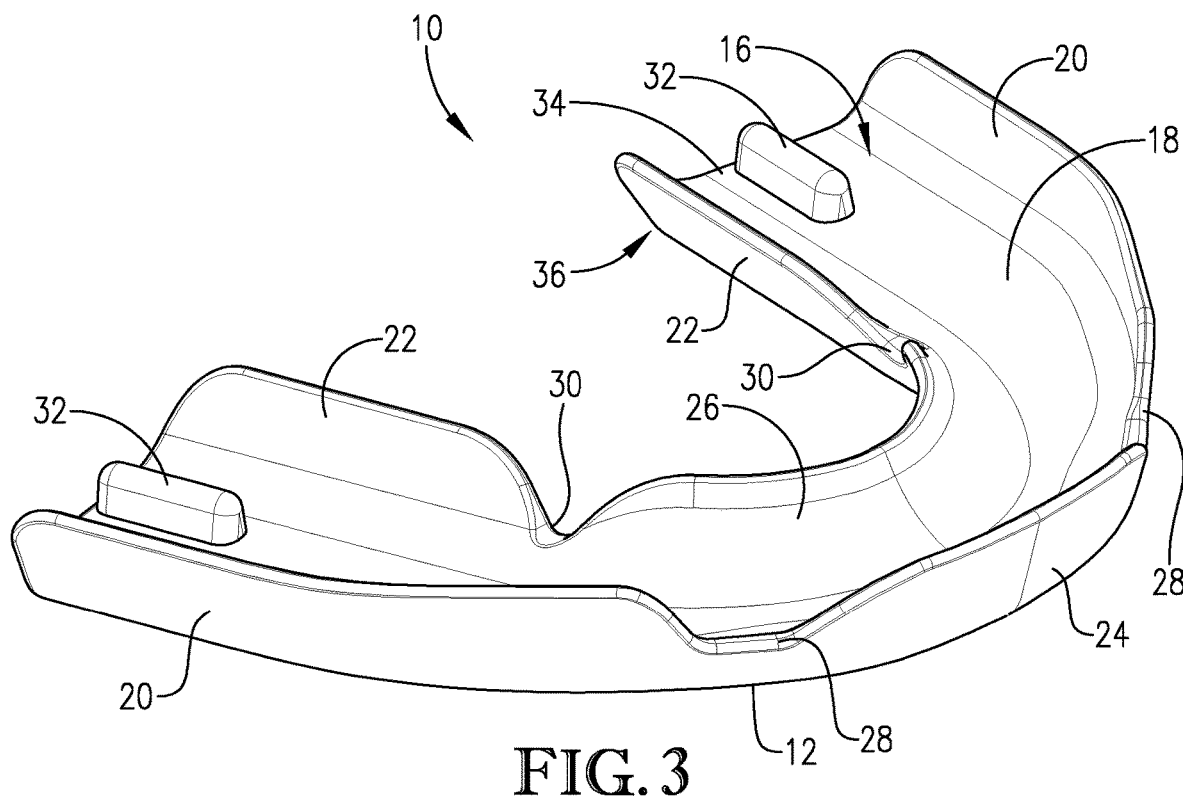
FIG. 3 is a top isometric view of the dental guard of FIG. 1.
Figure 4:
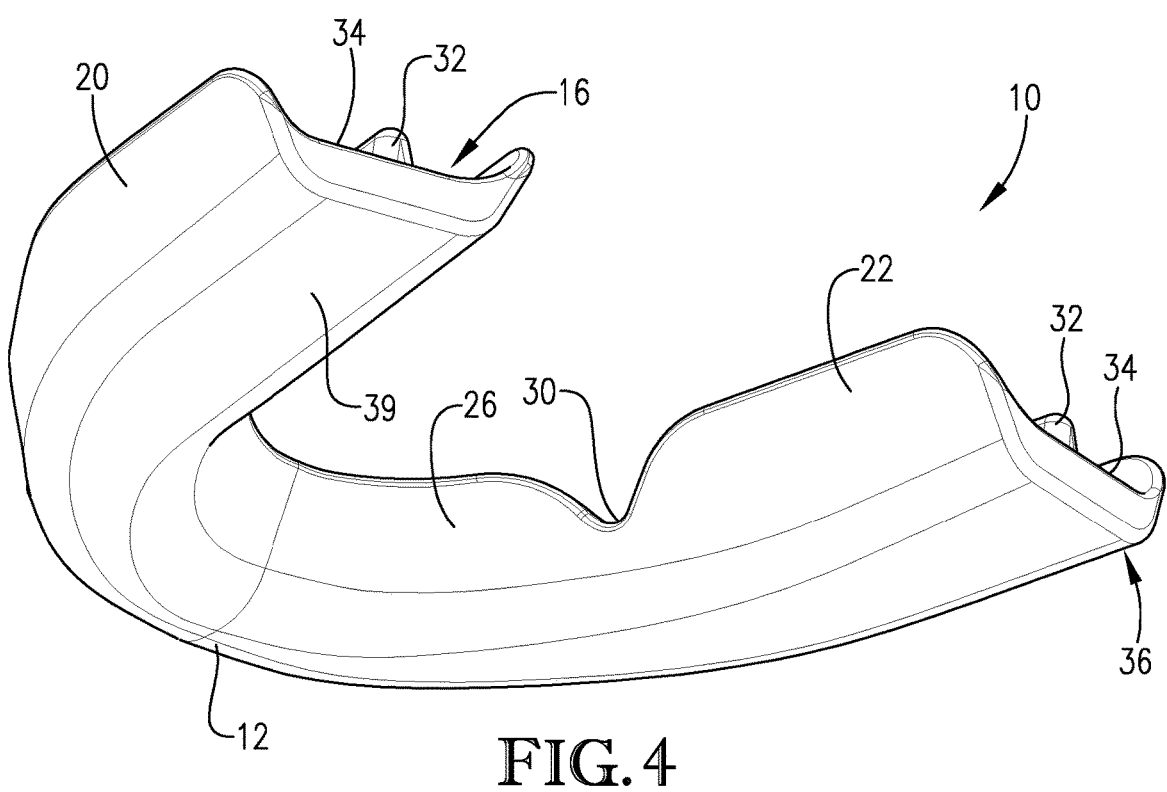
FIG. 4 is a bottom isometric view of the dental guard of FIG. 1.

Turning now to FIGS. 3 and 4, the dental guard 10 is more clearly shown. Guard 10 comprises an outer layer 12 formed from a thermoplastic material. In certain embodiments, layer 12 is overmolded about an inner core 14 (see, FIG. 5), formed from a polymeric material that is different from the thermoplastic material comprising the outer layer. The outer layer 12 is configured to define, at least in part a channel 16 that is adapted to receive at least some of the maxillary teeth of a user. The channel 16 comprises a maxillary occlusal surface 18, and preferably buccal sidewalls 20 and lingual sidewalls 22. In certain embodiments, guard 10 further comprises a facial sidewall 24 and an anterior palatal sidewall 26. The various sidewalls that assist in defining channel 16, as explained in further detail below, are formable to the contours of the user's maxillary teeth during customization of the guard. Thus, guard 10 may further comprise labial recesses 28 in between buccal sidewalls 20 and the facial sidewall 24, and lingual recesses 30 in between lingual sidewalls 22 and anterior palatal sidewall 26. Recesses 28, 30 provide space into which the thermoplastic material comprising the various sidewalls may be displaced during custom fitting of guard 10. In addition, recesses 28, 30 also provide passageways for drainage of saliva from the channel 16, as necessary.

Figure 6:
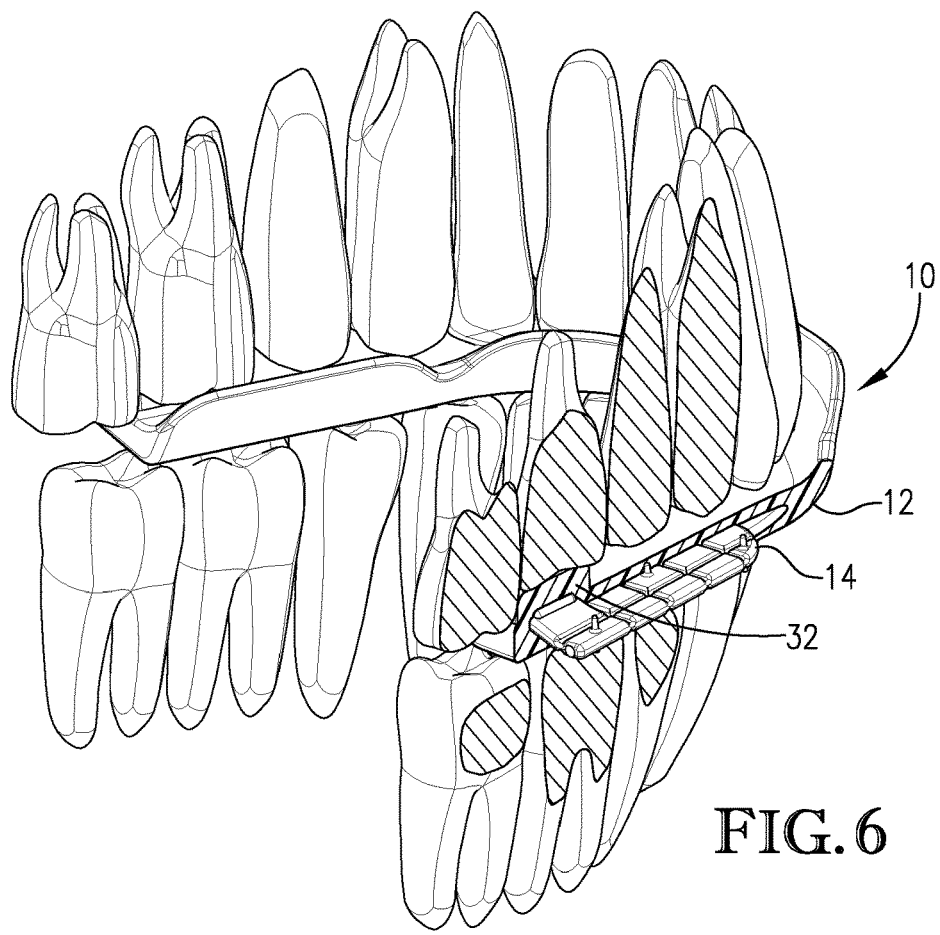
FIG. 6 is a sectioned view of the dental guard of FIG. 1 illustrating relative positioning of the guard and the user's teeth.

Positioning elements 32 extend upwardly from a posterior surface 34 of channel 16. As best seen in FIGS. 2 and 6, elements 32 are adapted to be received in the occlusal groove between the buccal and lingual cusps of a maxillary molar, preferably the first molar. It is also within the scope of the present invention for the positioning element 32 to extend downwardly from a posterior portion of a mandibular occlusal surface 39 of the dental guard 10, so that the positioning element is received in the occlusal groove between the buccal and lingual cusps of a mandibular molar. As explained in greater detail below, positioning elements 32 assist with proper alignment of guard 10 within the user's mouth during the custom-forming process. In certain embodiments, positioning elements 32 comprise a raised rib formed from the thermoplastic material of the outer layer 12. However, as explained below, positioning element may also comprise structures belonging to the core 14.

As noted above, in certain embodiments guard 10 comprises core 14 formed from a polymeric material that is different than the thermoplastic material comprising outer layer 12. In particular embodiments, the core material has a softening point temperature that is higher than the softening point temperature of the thermoplastic material of the outer layer 12. As used herein, the term "softening point temperature" can refer to the melting point of the particular material, or, the temperature at which the material otherwise loses its rigidity and becomes highly pliable and capable of being molded to the contours of a user's teeth. In certain embodiments, the thermoplastic material of the outer layer 12 has a softening point temperature of less than 90° C., less than 80° C., or less than 70° C. In alternate embodiments, the thermoplastic material of the outer layer 12 has a softening point temperature of from about 40° C. to about 80° C., about 45° C. to about 75° C., or from about 50° C. to about 70° C. In preferred embodiments, the thermoplastic material of the outer layer 12 has a softening point temperature of about 60° C. In certain embodiments, the polymeric material of the core 14 has a softening point temperature of at least 80° C., at least 85° C., or at least 100° C.

In certain embodiments, the outer layer 12 comprises polycaprolactone and the core 14 comprises a polyurethane resin material. Other suitable materials for the outer layer include various thermoplastic polyurethanes, and other suitable materials for the core include various polypropylene materials. In addition, core 14 may be formed from a polycaprolactone material or resin blend similar to that used in the outer layer; however, in such embodiments, the core polycaprolactone material would have a different melt profile temperature than that used for the outer layer. In certain embodiments, the core polycaprolactone material may be blended with other resins such as polypropylene, ethylene vinyl acetate, and/or polyethylene. In certain embodiments, the resin added to the polycaprolactone functions to reduce the crystallinity of the material following the injection molding process and/or other thermal processing of the guard that results in softening or melting of the polycaprolactone material, such as the custom fitting of the guard by the end user. Reducing the crystallinity avoids or lessens the shrinkage of the material following any thermal processing of the dental guard. In one particular embodiment, the core comprises a substantially homogeneous 70/30 blend of polycaprolactone/ethylene vinyl acetate. The core may also comprise a polyurethane, polypropylene, polyester, or methacrylate resin material. In certain embodiments, the outer layer 12 and/or core 14 may comprise additives or reinforcing materials embedded within the plastic and/or resin materials making up the respective structure thereby improving one or more physical properties of the materials, such as increasing the tensile strength, lowering the material melting point, lowering the coefficient of friction for the material, or interfering with the crystallization of the materials. For example, the materials may include glass or polytetrafluoroethylene additives that can improve the abrasion resistance of the material. Exemplary additives in this regard include glass fibers or particles, polytetrafluoroethylene, fluorinated ethylene propylene, starches, talc, calcium silicates, calcium carbonate and foaming additives, such as FOAMAZOL 90 (a blend of citric and carbonic salts). Of course, other additives may be added to the plastic or resin materials in order to impart desired characteristics as known and expected by one skilled in the art. For example, water could be added to the polycaprolactone material in order to inhibit crystallization of the polycaprolactone during manufacture. The polymeric core material is highly durable and resistant to wear caused by contact with the user's teeth during use of the dental guard 10. In certain embodiments, core 14 makes guard 10 at least 10 times more durable that conventional dental guards.

Figure 5:
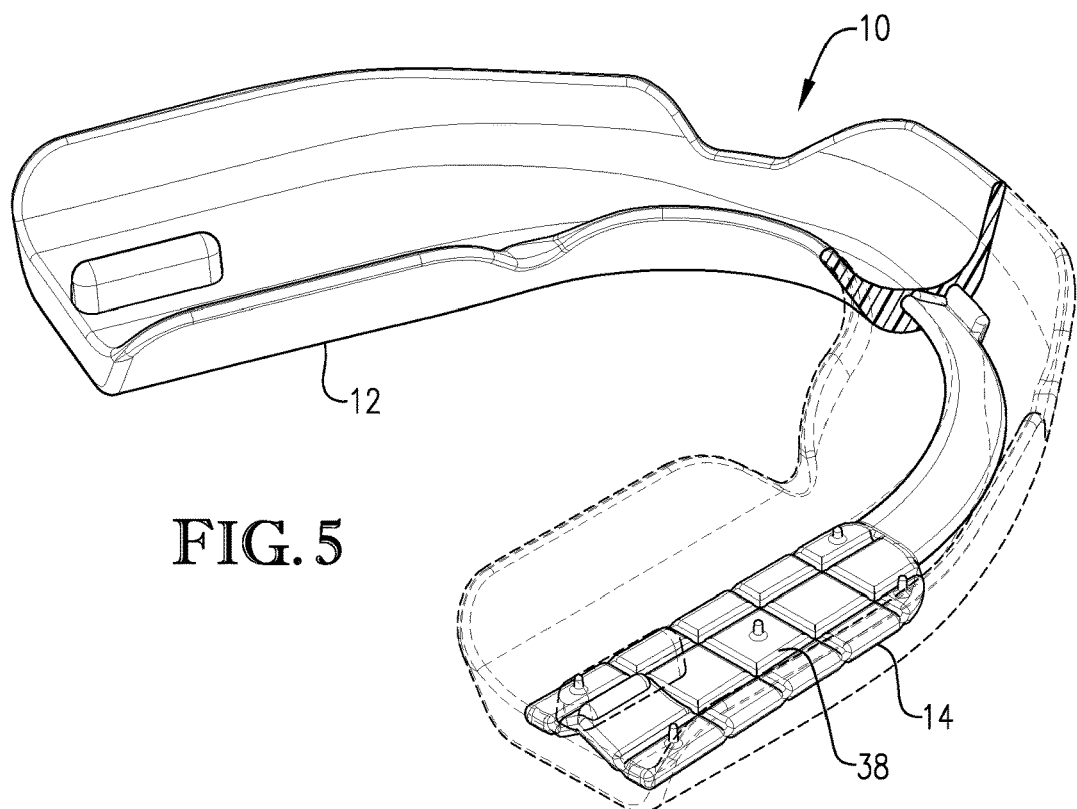
FIG. 5 is a sectioned isometric view of the dental guard of FIG. 1

FIG. 5 illustrates the core/outer layer construction of a dental guard 10 made in accordance with the present invention. Core 14 is overmolded with the thermoplastic material comprising outer layer 12. As best seen in FIGS. 8-10, core 14 generally comprises a pair of bite pads 38 interconnected by an anterior arch segment 40. It is noted that arch segment 40 and bite pads 38 need not necessarily be in the form of discrete components, but rather they can form unitary sections of a core structure that do not have well-defined transitional segments between said sections. It is also within the scope of the present invention for the arch segment 40 to not be continuous with bite pads 38. Rather, arch segment 40 may be disposed in between bite pads and separated therefrom by, for example, the same material which comprises outer layer 12. Each of bite pads 38 comprise opposed maxillary 42 and mandibular 44 occlusal surfaces. These surfaces are configured to be overmolded by portions of outer layer 12 that are configured to contact the user's maxillary and mandibular teeth, respectively. In order to assist with the overmolding process, a plurality of offsets 46a, 46b extend from respective maxillary and mandibular occlusal surfaces. These offsets are configured to provide space within the mold of an injection molding machine for the thermoplastic material of the outer layer to flow around and substantially cover or envelop the occlusal surfaces 42, 44 of bite pads 38. In certain embodiments, it is desired for the portion of the outer layer 12 comprising the channel 16 to be thicker than the opposed portion of outer layer 12 configured to contact the user's mandibular teeth. In order to accomplish this, offsets 46a may be greater in length than offsets 46b. Upon overmolding of core 14, offsets 46a, 46b are also covered by the thermoplastic material of the outer layer 12. In certain embodiments, the entire maxillary 42 and mandibular occlusal 44 surfaces are covered by the thermoplastic material.

As illustrated in FIG. 6, the bite pads 38 are configured such that the mandibular 44 and maxillary 42 occlusal surfaces reside between at least the first molar and the proximal pre-molar mandibular and maxillary teeth when guard 10 is placed within the user's mouth. In other embodiments (not shown), the bite pads are configured such that at least a portion of the maxillary 42 and mandibular 44 occlusal surfaces reside between the second molars and first bicuspids when guard 10 is placed within the user's mouth.

In certain embodiments, the anterior arch segment 40 comprises spaced apart end sections 48 that are coupled to bite pads 38. The end sections are interconnected by mesial sections 50 that meet at a midline section 52. In certain embodiments, at least a portion of the maxilla-facing surfaces of mesial sections 50 resides in a plane that is different from the plane in which at least one of bite pads 38, and in particular the maxillary occlusal surface 42, resides. In particular embodiments, the relative angle between these two planes is from about 20° to about 50°, or from about 25° to about 40°, or from about 30° to about 35°. Moreover, in certain embodiments, each of the bite pads 38 has a thickness that is greater than the thickness of at least a portion of arch segment 40, in particular, mesial sections 50. However, it is within the scope of the present invention for arch segment 40 to have a similar or the same thickness as each bite pad 38.

In certain embodiments of the present invention, each of bite pads 38 may comprise one or more hinges 54, 64 formed therein that divide the bite pads into respective bite pad segments 58. The one or more hinges permit pivoting of at least one bite pad segment relative to another bite pad segment, which provides for enhanced customization of the dental guard fit to the user's occlusal pattern, which leads to greater comfort of use. These hinges may comprise a wide variety of configurations, such as those represented in the Figures. However, generally, the one or more hinges comprise areas of reduced thickness in the bite pads 38. In certain embodiments, hinges 54, 64 generally comprise a pair of superposed trenches 56; one trench being formed in the maxillary occlusal surface 42, and one trench being formed in the mandibular occlusal surface 44.

In the embodiment illustrated in FIGS. 8-10, the bite pads 38 comprise at least one, and preferably more than one, longitudinal hinge 54 and at least one, and preferably more than one, transverse hinge 64 configured as previously described. Hinges 54, 64 define a plurality of bite pad segments 58. Bite pads 38 further comprise a positioning rib 59 that comprises positioning element 32 in the finished dental guard 10. Positioning rib 59 extends upwardly from maxillary occlusal surface 42 of a posterior portion 68 of the bite pad. As can be seen, rib 59 is oriented such that its length runs longitudinally with respect to bite pad 38. When overmolded with the outer layer 12, rib 32 comprises the base for positioning element 32, which as previously mentioned, is adapted to be received in the occlusal groove between the buccal and lingual cusps of a maxillary molar, thereby assisting the user with proper alignment of the guard during the custom fitting process.

The rib 59 is elevated above the main maxillary occlusal surface 42 and extends from a peaked segment 72 formed in the posterior portion 68 of bite pad 38. This peaked segment 72 comprises sloped sections 74, 75 that intersect at an angle, preferably an obtuse angle, although the angle may be acute or right. As illustrated, section 74 has a greater width than section 75, which serves to offset rib 59 toward the lingual side of bite pads 38.

Figure 11:
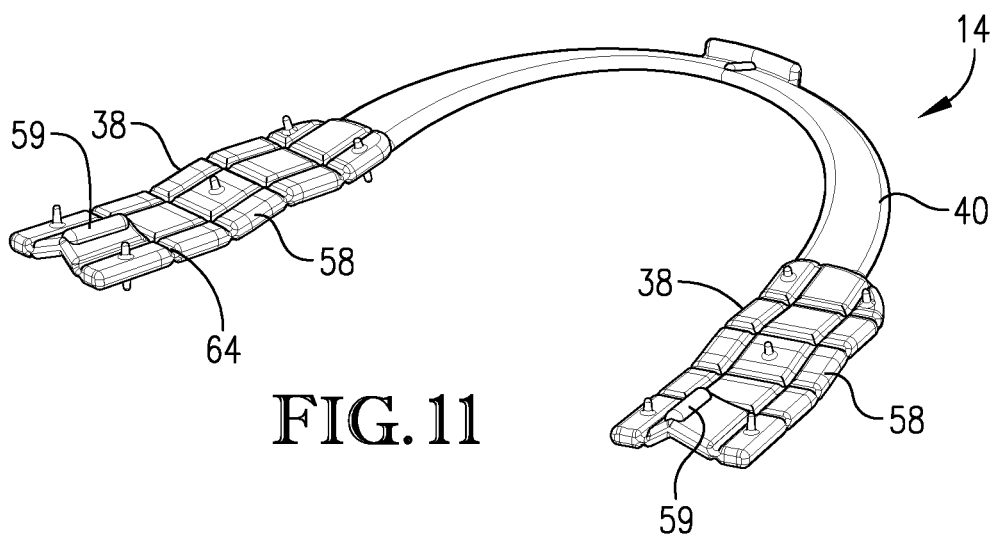
FIG. 11 is an isometric view of the core utilized in the dental guard of FIG. 1 showing relative pivoting of certain bite pad segments as might occur during the custom fitting process.
Figure 12:
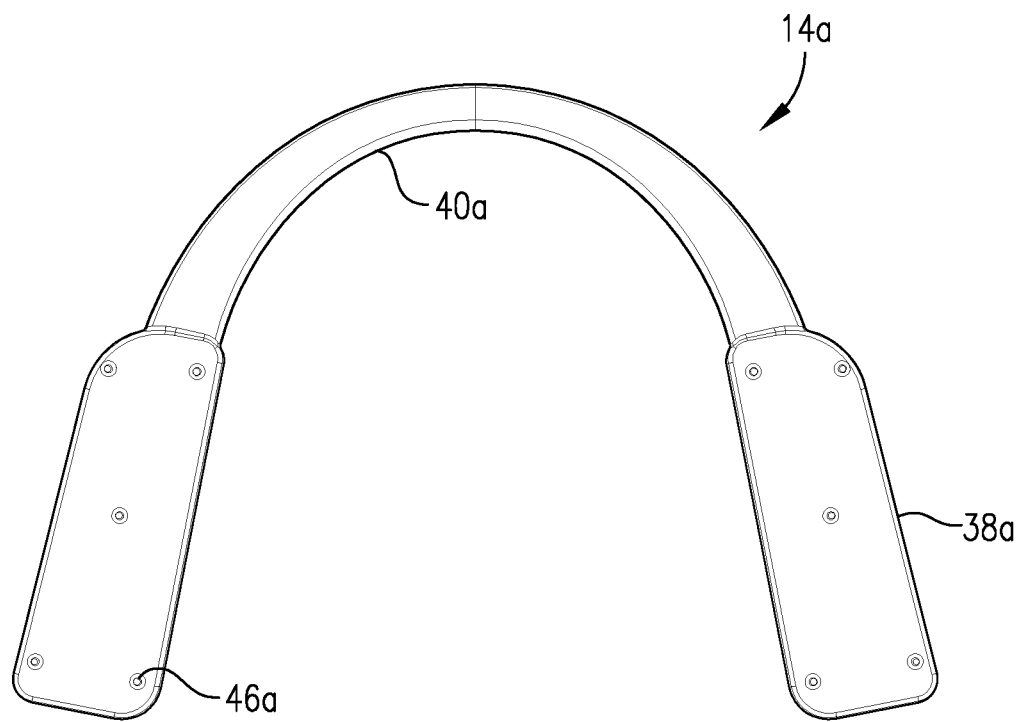
FIG. 12 is a top plan view of another embodiment of a core that may be utilized in the construction of a dental guard according to the present invention.
Figure 13:
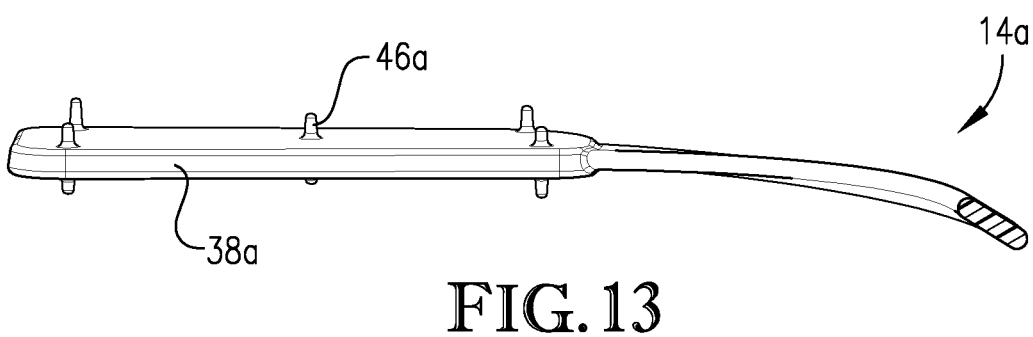
FIG. 13 is a sectioned perspective view of the core of FIG. 12.
Figure 14:
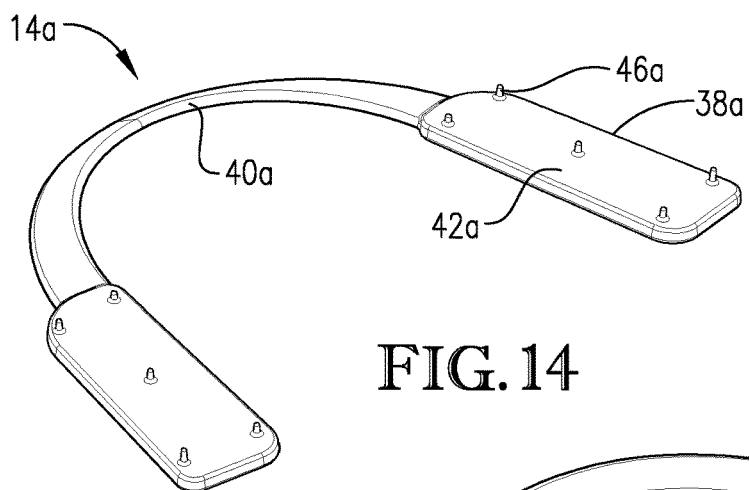
FIG. 14 is a top isometric view of the core of FIG. 12.
Figure 15:
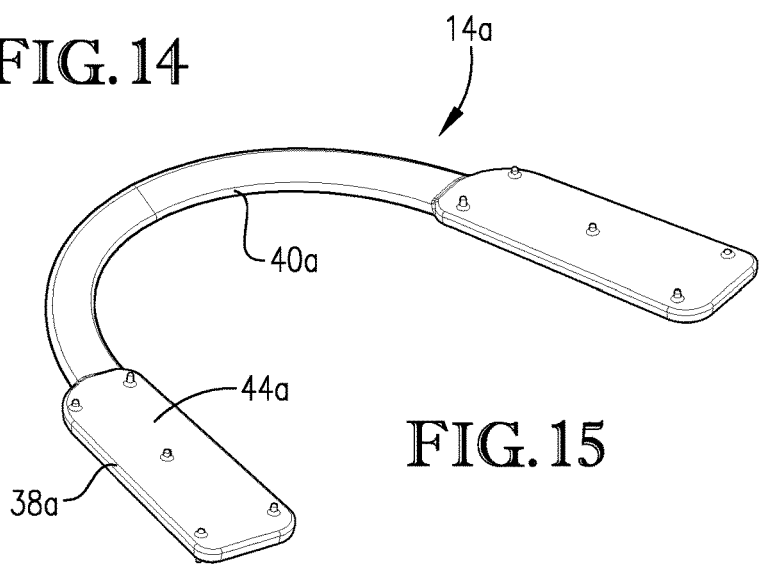
FIG. 15 is a bottom isometric view of the core of FIG. 12.

FIG. 11 depicts core 14 exhibiting pivoting of bite pad segments 58 about hinges 64 thereby illustrating that core 14 can be conformed to a particular user's occlusal pattern. The ability to customize core 14 to a specific user's bite enhances the custom fit of the dental guard 10 and increases the user's comfort in wearing the guard.

In embodiments in which core 14 is formed from a softer material such as polypropylene, hinges 54, 64 form living hinges that are capable of numerous flexures without experiencing failure through material fatigue. Living hinges formed of polypropylene or a similar material are more easily conformable to the user's bite during the custom fitting process. These hinges become "frozen" into position upon re-solidification of outer layer 12, which is described in greater detail below.

Core 14 further comprises additional features located on the anterior arch segment 40 that further help to positioning guard 10 within the user's mouth during custom fitting. Core 14 comprises an anterior locating feature 84 that includes a rib 85 formed in the midline of the anterior arch segment 40. Rib 85 is sized so as to be at least partially received in the interproximal space between the user's central maxillary teeth. Locating feature 84 further includes a lip segment 90 that extends from a front edge 88 of arch segment 40 in a superior direction. As explained below, locating feature 32 and anterior locating feature 84 cooperate to ensure that the user correctly positions the dental guard around his or her maxillary teeth during the custom fitting process.

Dental guard 10 may be custom-fitted to the user's mouth so as to provide a custom-formed guard that approximates the fit of a clinical dental guard. Custom fitting begins by heating the dental guard to a temperature less than the boiling point of water, preferably no greater than 85° C., and more preferably between about 40° C. to about 80° C. in order to soften at least a portion of the dental guard 10, particularly outer layer 12. Heating of the dental guard 10 may be accomplished by immersing the guard in hot, but not boiling, water. The hot water may be obtained from the hot water tap connected to a typical residential water heater. Alternatively, tepid water can be heated, for example, in a microwave oven until it reaches the desired temperature, which should be very close to the softening point temperature of the thermoplastic material forming the outer layer 12. In certain embodiments, upon reaching the softening point temperature, outer layer 12 turns translucent (whereas below the softening point temperature outer layer 12 is opaque). At this point, the user can be assured that the guard 10 has been heated sufficiently.

The user then places the softened dental guard within his or her mouth and positions the guard so that at least some of the user's maxillary teeth reside within and contact at least one surface the channel 16. In addition, positioning element 32, if present, may be placed within the occlusal groove between the buccal and lingual cusps of a maxillary or mandibular molar. Also, anterior locating feature 84, may be utilized at this time. The user can ensure that rib 85 is placed in the interproximal space between the user's central maxillary teeth to prevent lateral movement of the guard, and that lip segment 90 contacts the vestibular portions of the user's central incisors thereby forming a positive stop to prevent further insertion of the guard into the user's mouth.

The user then brings the mandibular teeth into contact with mandibular occlusal surface 39. Because outer layer 12 is soft and pliable, outer layer 12, and especially maxillary occlusal surface 18 and mandibular occlusal surface 39 conform to the occlusal surfaces of the mandibular and maxillary teeth of the user. As illustrated in FIGS. 7b and 7c, the occlusal groove in the user's molar M may not precisely align with positioning element 32. Rather, the element may be skewed toward the buccal or lingual cusps. However, so long as at least a portion of positioning element 32 is received within the occlusal groove, as the user's mandibular teeth are brought into contact with mandibular occlusal surface 39, the portion of outer layer 12 overlying rib 59 is displaced and the rib is directed along the surface of the occlusal groove until element 32 rests fully within the groove. The user may also apply pressure to the various sidewalls 20, 22, 24, and 26 so that the sidewalls conform to the vestibular and palatal portions of the user's maxillary teeth, again, giving the dental guard 10 a clinical fit. Before removing the guard from his or her mouth, the user permits the softened outer layer to cool below its softening point temperature and harden.

FIGS. 12-61 depict alternate core and guard embodiments according to the present invention. For the sake of being concise, only those features that set the alternate core and guard embodiments apart from each other are discussed and those features common to the various core and guard embodiments, while present, are not re-discussed. It is also understood that these core and guard embodiments are provided by way of illustration and should not be taken as limiting upon the scope of the present invention. Moreover, it is understood that any individual features of each core or guard may be combined with the features of other core or guard embodiments as desired to suit the needs of a particular dental guard application.

Turning first to FIGS. 12-15 core 14a represents a greatly simplified version of core 14 in which bite pads 38a comprise only the plurality of offsets 46a extending from the maxillary 42a and mandibular 44a occlusal surfaces. Bite pads 38a are interconnected by anterior arch segment 40a, but do not include an anterior locating feature 84 as with core 14.

Figure 16:
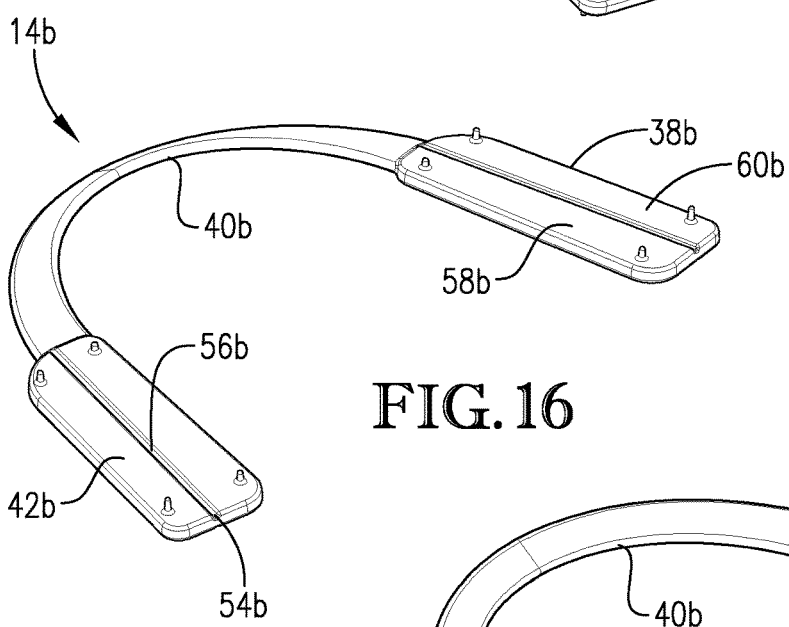
FIG. 16 is a top isometric view of another embodiment of a core that may be utilized in the construction of a dental guard according to the present invention having a longitudinal hinge formed in each bite pad.
Figure 17:
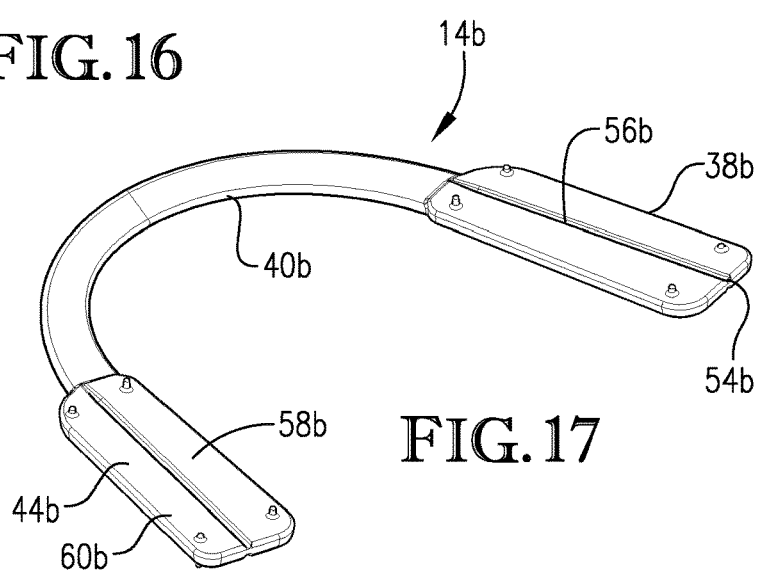
FIG. 17 is a bottom isometric view of the core of FIG. 16.

FIGS. 16 and 17 illustrate another embodiment of a core 14b that comprises bite pads 38b interconnected by an anterior arch segment 40b. Bite pads 38b comprise a hinge 54b that is of longitudinal configuration relative to the bite pad 38b. In other embodiments, hinge 54b may be substantially contiguous with the longitudinal bite pad. As with previously described hinges 54, hinges 54b comprise a pair of superposed trenches 56b; one trench being formed in the maxillary occlusal surface 42b, and one trench being formed in the mandibular occlusal surface 44b. Hinge 54b divides bite pad 38b into respective bite pad segments 58b, 60b.

Figure 18:
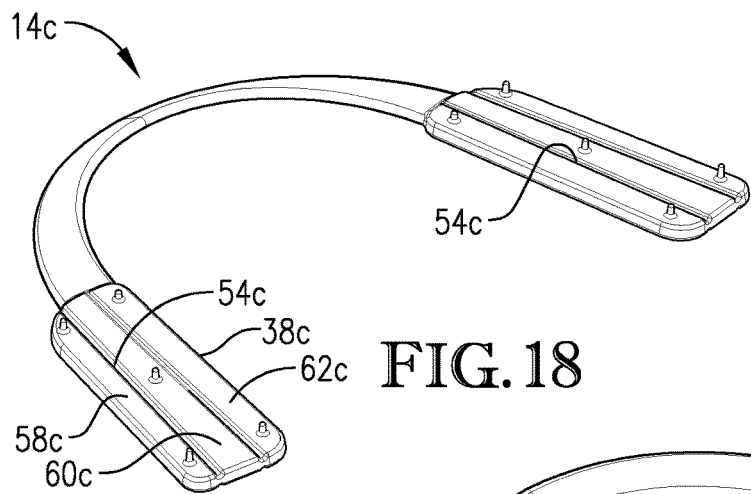
FIG. 18 is a top isometric view of another embodiment of a core that may be utilized in the construction of a dental guard according to the present invention having a pair of longitudinal hinges formed in each bite pad.
Figure 19:
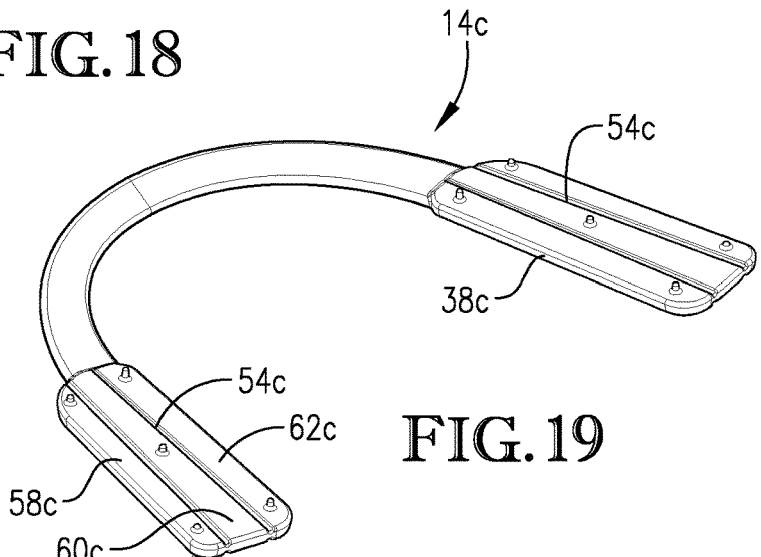
FIG. 19 is a bottom isometric view of the core of FIG. 18.

FIGS. 18 and 19 illustrate another embodiment of a core 14c. This embodiment is very similar to core 14b of FIGS. 16 and 17, except that bite pads 38c each comprise two longitudinal hinges 54c that divide bite pad 38c into segments 58c, 60c, and 62c. In certain embodiments, at least one of hinges 54c may be substantially parallel to a longitudinal axis of bite pad 38c; however, it is within the scope of the present invention for at least one of hinges 54c to be oriented at an oblique angle to the longitudinal axis of the bite pad.

Figure 20:
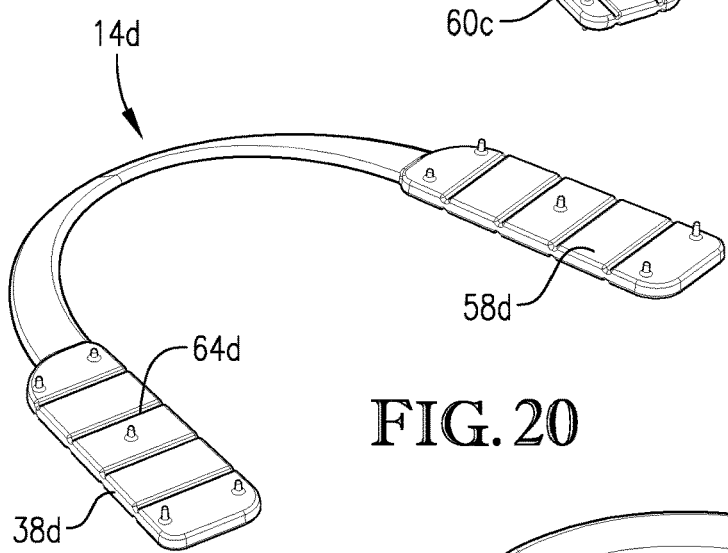
FIG. 20 is a top isometric view of another embodiment of a core that may be utilized in the construction of a dental guard according to the present invention having a plurality of transverse hinges formed in each bite pad.
Figure 21:
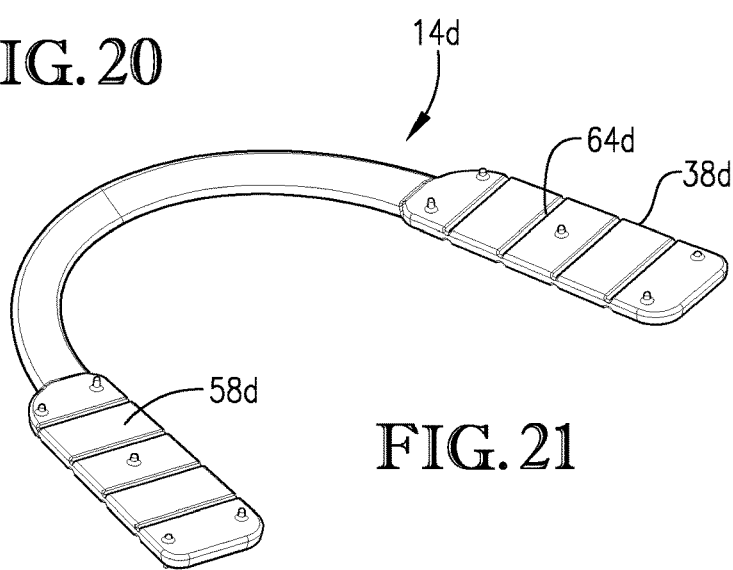
FIG. 21 is a bottom isometric view of the core of FIG. 20.

FIGS. 20 and 21 illustrate another embodiment of a core 14d. Core 14d comprises a plurality of hinges 64d that are oriented transversely to a longitudinal axis of the respective bite pads 38d and divide the bite pads into a plurality of bite pad segments 58d.

FIGS. 22 and 23 illustrate a further embodiment of a core 14e. Core 14e comprises bite pads 38e that have a combination of longitudinal hinges 54e and transverse hinges 64e, which divide the bite pads into a plurality of bite pad segments 58e.

FIGS. 24 and 25 illustrate a further embodiment of a core 14f. Core 14f is substantially similar to core 14e, except that core 14f further comprises a plurality of tines 76 that extend from the bite pad sidewall 78 in a superior direction. Bite pads 38f may comprise tines 76 on both the buccal and lingual sides thereof. Tines 76 comprise locating features to assist with positioning of the dental guard within the user's mouth during the custom fitting process. Tines 76 are flexible and configured to clasp onto the buccal and lingual sides of the user's maxillary molars, especially, the user's first molars. Alternatively, tines 76 may be configured to rest within an interproximal space between at least one of the user's molars and an adjacent tooth.

Figure 26:
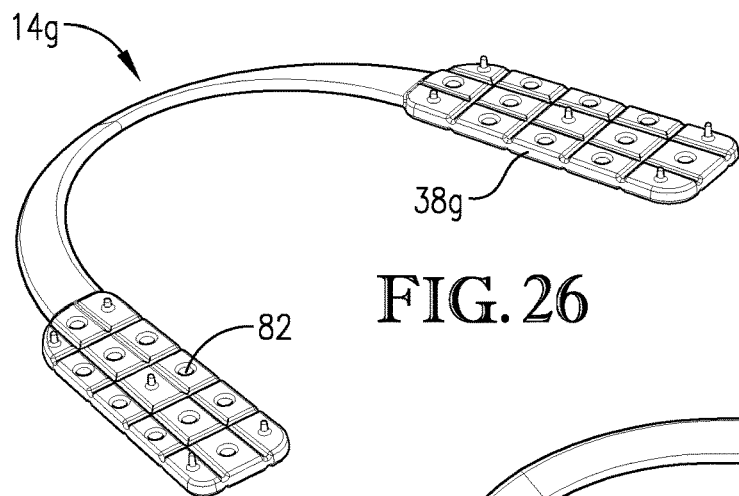
FIG. 26 is a top isometric view of another embodiment of a core that may be utilized in the construction of a dental guard according to the present invention having a plurality of openings formed in each bite pad.
Figure 27:
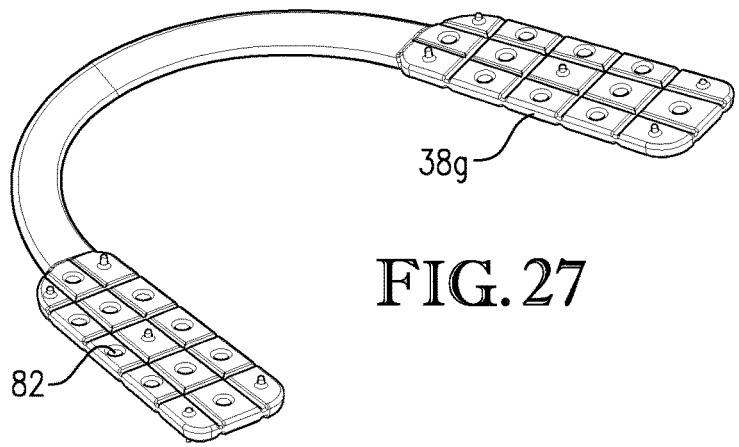
FIG. 27 is a bottom isometric view of the core of FIG. 26.

FIGS. 26 and 27 illustrate still a further embodiment of a core 14g. Core 14g comprises bite pads 38g having a plurality of openings 82 formed therein. The openings 82 permit the thermoplastic material comprising the outer layer 12 to flow therethrough during the overmolding process enhancing the adhesion between the outer layer and core 14g.

Figure 28:
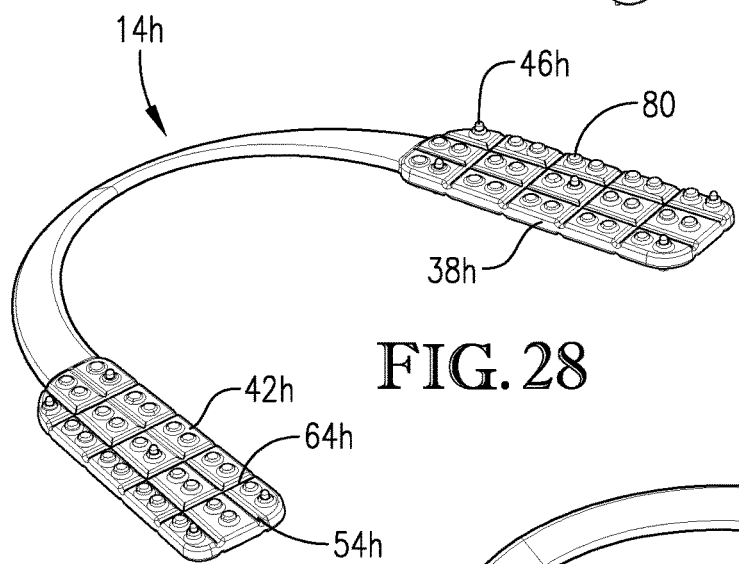
FIG. 28 is a top isometric view of another embodiment of a core that may be utilized in the construction of a dental guard according to the present invention having a plurality of raised buttons extending from the surface of each bite pad and including a plurality of offsets extending above the upper margins of certain buttons.
Figure 29:
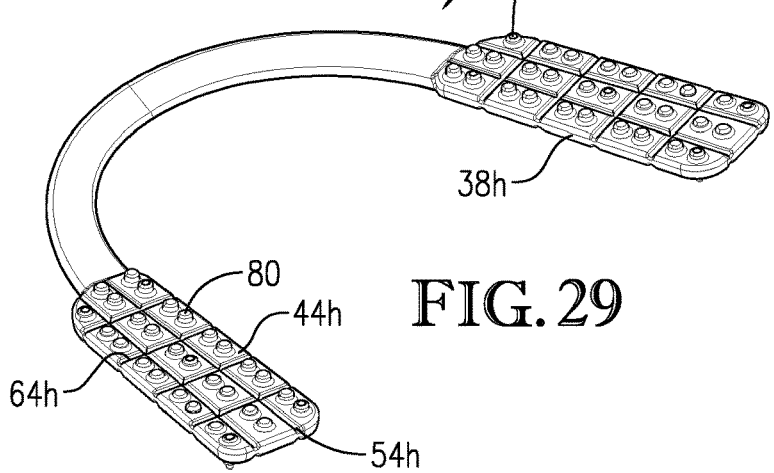
FIG. 29 is a bottom isometric view of the core of FIG. 28.

FIGS. 28 and 29 illustrate yet another embodiment of a core 14h. Core 14h comprises bite pads 38h having a plurality of buttons 80 extending from both the maxillary occlusal surface 42h and mandibular occlusal surface 44h. Buttons 80 increase the overall surface area of the occlusal surfaces 42h, 44h to provide for better adhesion retention between core 14h and the overmolded outer layer 12. Buttons 80 also increase the overall durability of core 14h during use of the dental guard while still allowing for flexing of bite pads 38h about hinges 54h, 64h. In certain embodiments, buttons 80 have a height that is less than that of the offsets 46h as it can be seen that certain offsets 46h extend beyond buttons 80.

Figure 30:
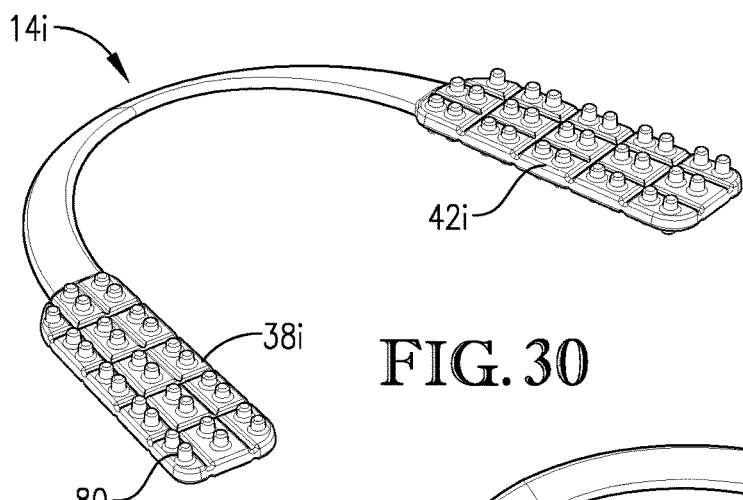
FIG. 30 is a top isometric view of another embodiment of a core that may be utilized in the construction of a dental guard according to the present invention having a plurality of raised buttons extending from the surface of each bite pad.
Figure 31:
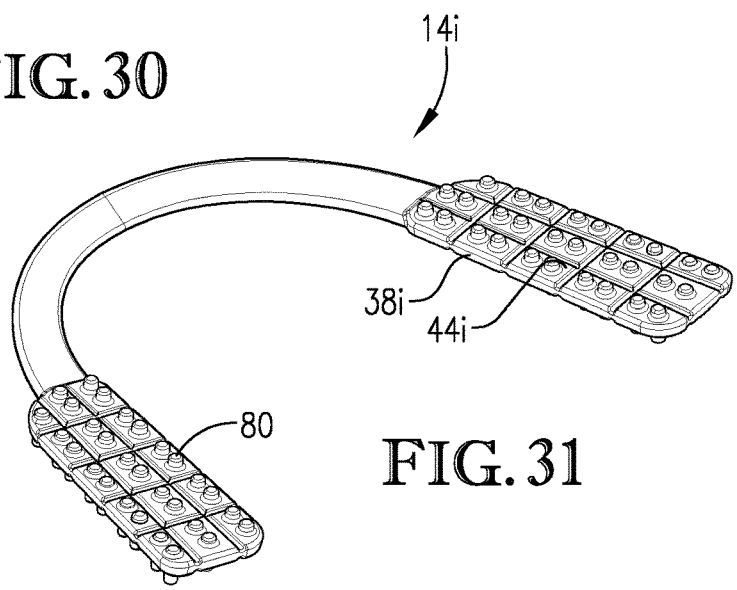
FIG. 31 is a bottom isometric view of the core of FIG. 30.

FIGS. 30 and 31 illustrate an embodiment of a core 14i that is similar to core 14h of FIGS. 28 and 30 except that offsets 46h have been removed leaving buttons 80 as the only structures that extend from the occlusal surfaces 42i, 44i of bite pads 38i.

Figure 32:
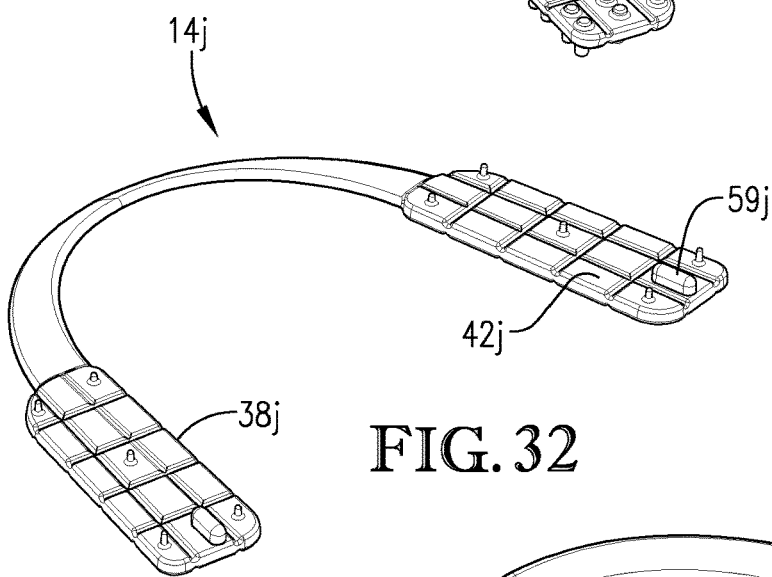
FIG. 32 is a top isometric view of another embodiment of a core that may be utilized in the construction of a dental guard according to the present invention having a positioning element extending from the maxillary occlusal surface of each bite pad.
Figure 33:
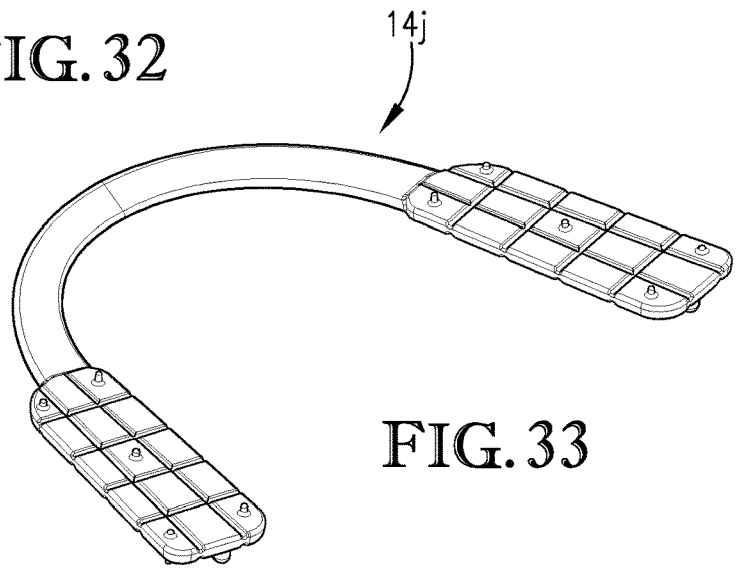
FIG. 33 is a bottom isometric view of the core of FIG. 32.

FIGS. 32 and 33 illustrate an embodiment of a core 14j that is similar to core 14e of FIGS. 22 and 23. Core 14j further comprises a positioning rib 59j that extends from the mandibular occlusal surface 42j of bite pads 38j. Much like rib 59 of core 14, and once core 14j is overmolded with outer layer 12, rib 59j comprises a positioning element similar to positioning element 32.

FIGS. 34 and 35 illustrate an embodiment of a core 14k that similar to core 14j, however the posterior portion 36k of bite pads 38k comprises sloped segments 74k, 75k. Rib 59k extends from the junction of sloped segments 74k, 75k. It is also noted that sloped segments 74k, 75k are generally symmetrical thereby positioning rib 59k centrally with respect bite pads 38k. In addition, longitudinal hinges 54k do not extend through sloped segments 74k, 75k.

FIGS. 36 and 37 illustrate an embodiment of a core 14l that is similar to core 14k, except that hinges 54l extend the full length of bite pads 38l. In addition, sloped segments 74l, 75l are shortened and reside in between adjacent hinges 54l.

Figure 38:
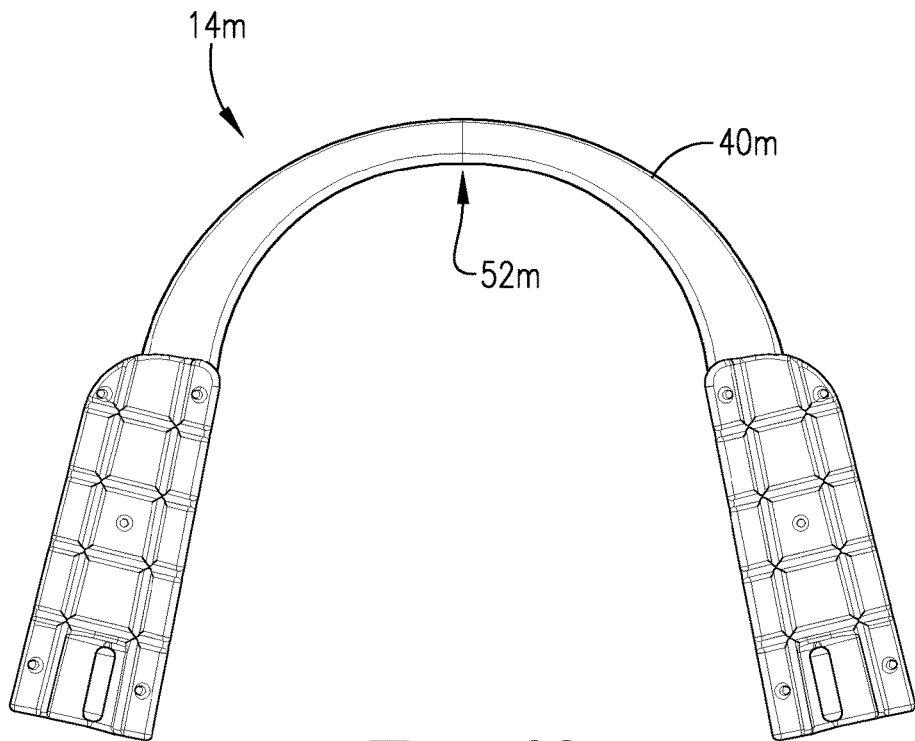
FIG. 38 is a top plan view of another embodiment of a core that may be utilized in the construction of a dental guard according to the present invention having an offset positioning element formed in a raised posterior portion of the bite pad.
Figure 39:
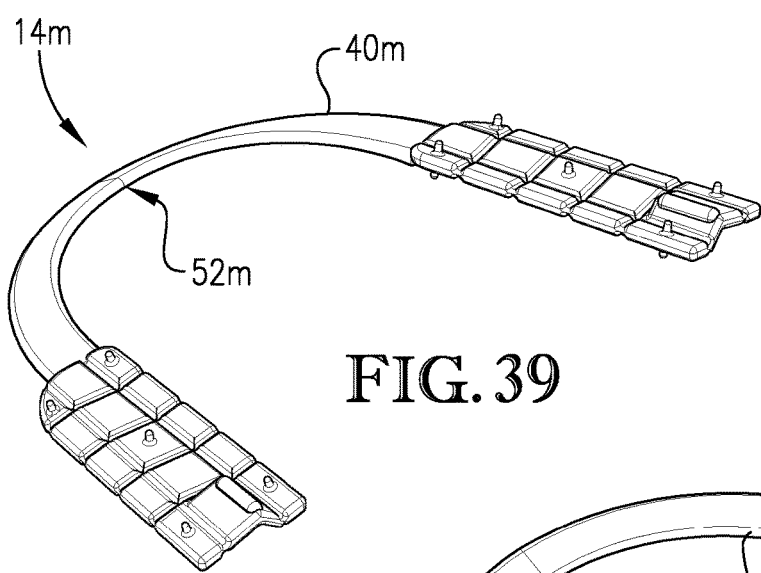
FIG. 39 is a top isometric view of the core of FIG. 38.
Figure 40:
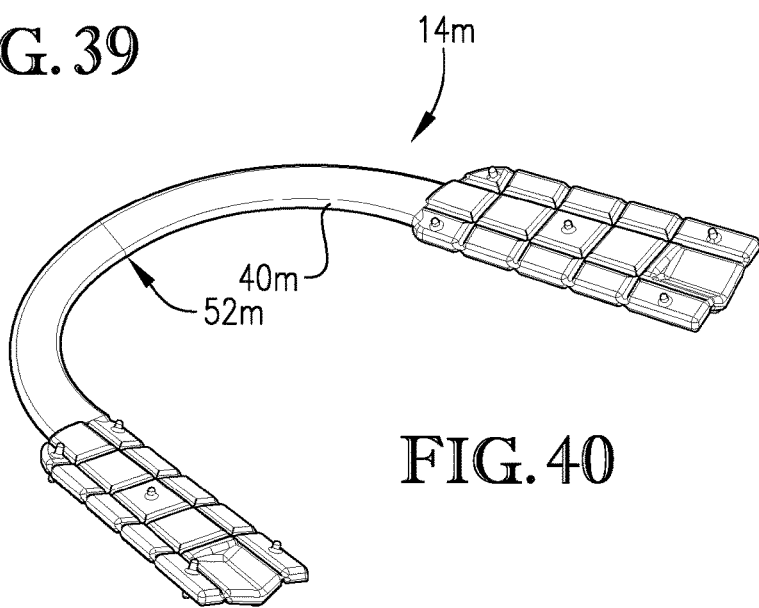
FIG. 40 is a bottom isometric view of the core of FIG. 38.

FIGS. 38-40 illustrate an embodiment of a core 14m that is similar to core 14, except that anterior arch segment 40m has a flatter midline section 52m. Thus, the span of anterior arch segment 40m can be made wider without increasing the overall length of the core 14m.

Figure 41:
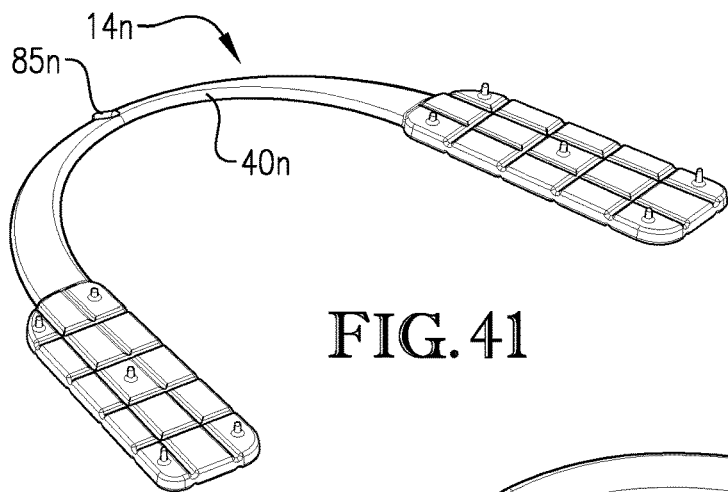
FIG. 41 is a top isometric view of another embodiment of a core that may be utilized in the construction of a dental guard according to the present invention having an anterior positioning element extending from the maxillary surface of the anterior arch segment.
Figure 42:
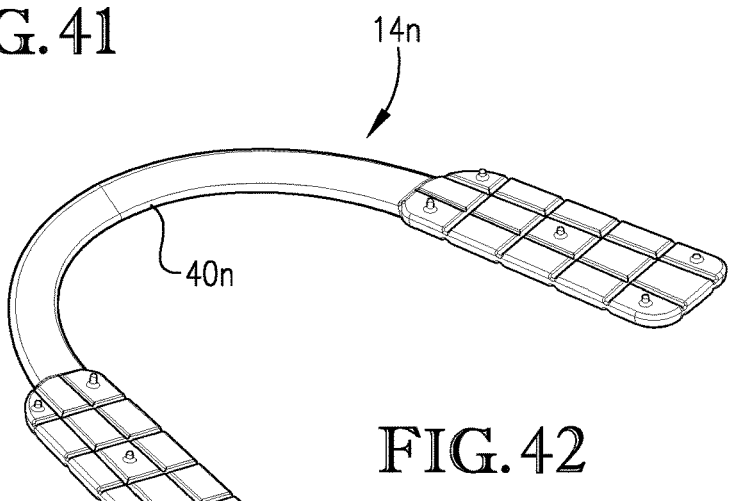
FIG. 42 is a bottom isometric view of the core of FIG. 41.

FIGS. 41 and 42 illustrate an embodiment of a core 14n that is similar to core 14e of FIGS. 22 and 23, except that anterior arch segment 40n comprises a rib 85n formed in the midline of the anterior arch segment 40n. Much like rib 85, rib 85n is sized so as to be at least partially received in the interproximal space between the user's central maxillary teeth to prevent lateral movement of the dental guard during the custom fitting process.

Figure 43:
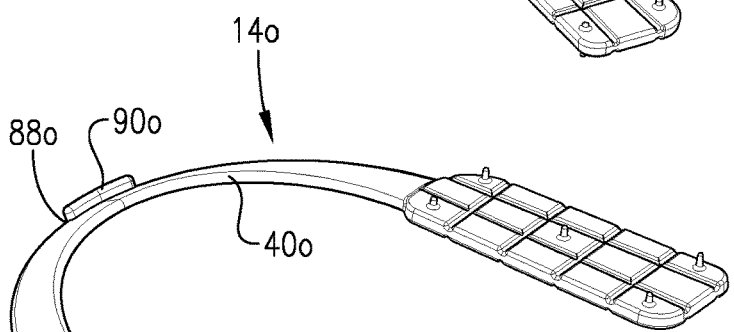
FIG. 43 is a top isometric view of another embodiment of a core that may be utilized in the construction of a dental guard according to the present invention having an anterior positioning element extending from the anterior arch segment and configured to engage the anterior surfaces of the user's central incisors.
Figure 44:
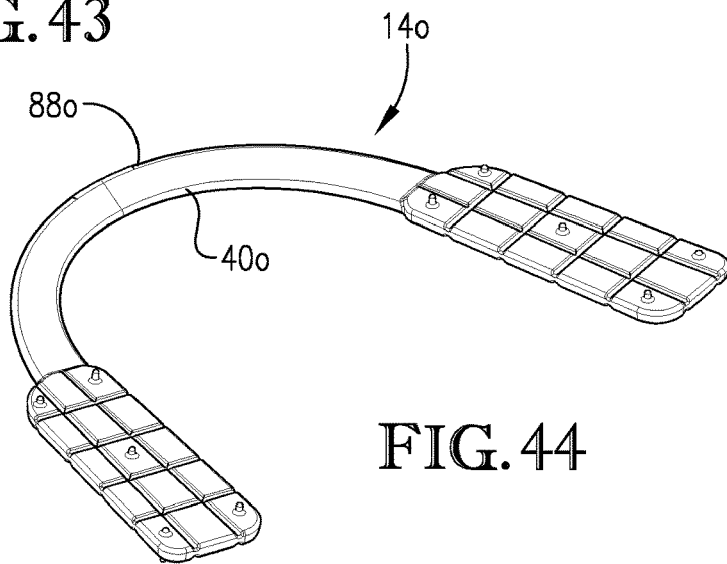
FIG. 44 is a bottom isometric view of the core of FIG. 44.
Figure 49:
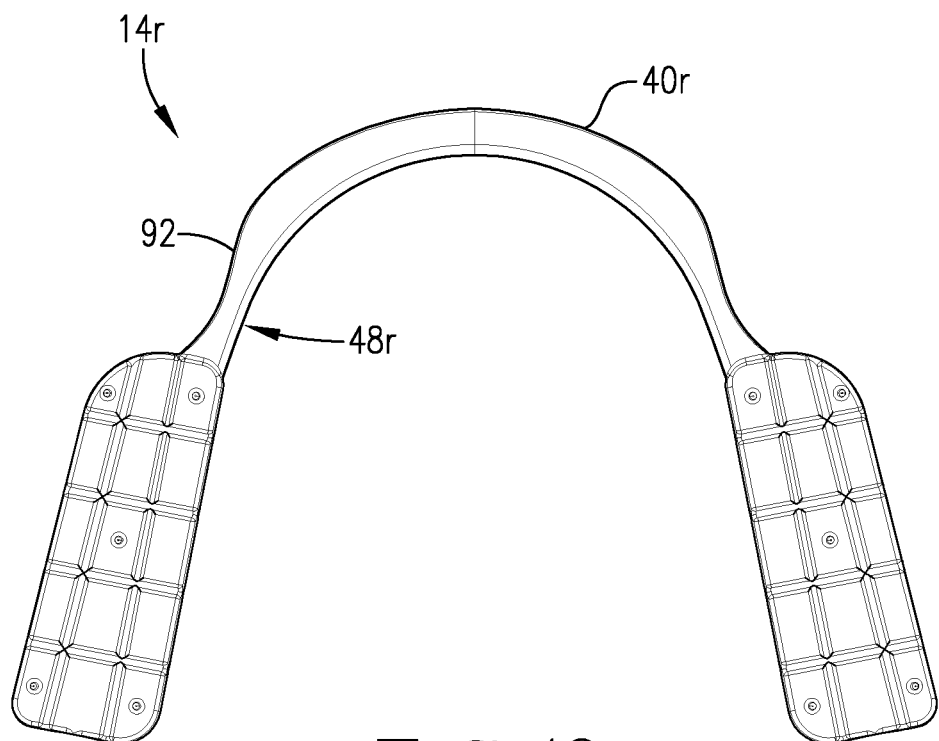
FIG. 49 is a top plan view of another embodiment of a core that may be utilized in the construction of a dental guard according to the present invention having a recessed posterior portion of the anterior arch segment so as to better accommodate the user's bicuspid teeth.
Figure 50:
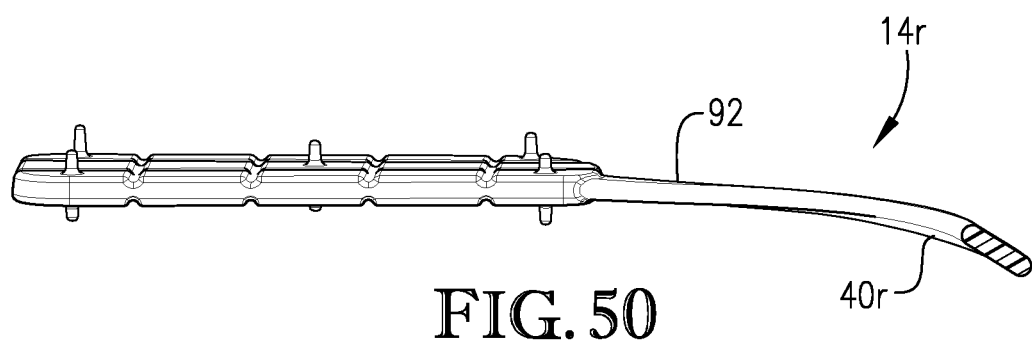
FIG. 50 is a sectioned perspective view of the core of FIG. 49.
Figure 51:
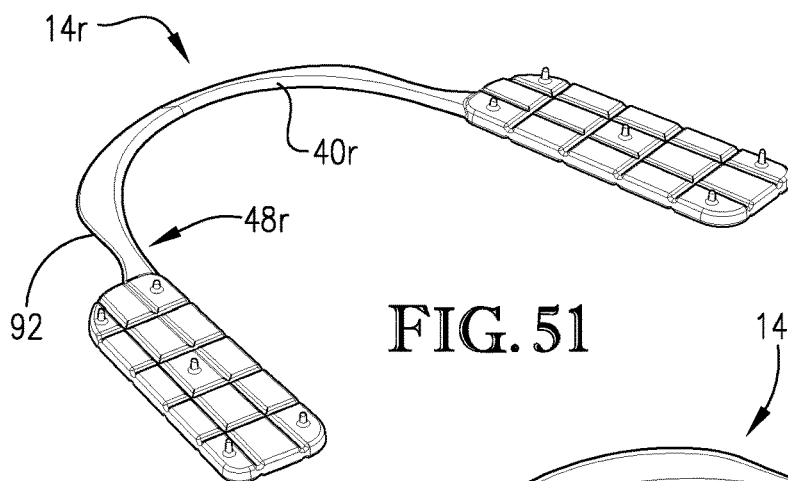
FIG. 51 is a top isometric view of the core of FIG. 49.
Figure 52:
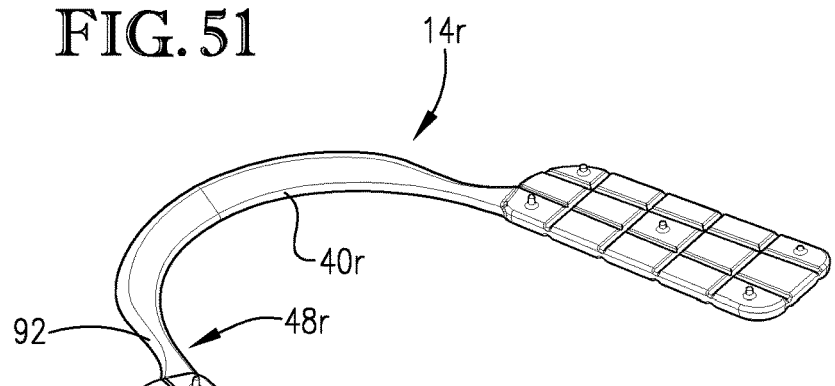
FIG. 52 is a bottom isometric view of the core of FIG. 49.

FIGS. 43 and 44 illustrate an embodiment of a core 14o that is similar to core 14e of FIGS. 22 and 23, except that anterior arch segment 14o comprises a lip segment 90o that extends from a front edge 88o of arch segment 40o in a superior direction. Much like lip segment 90 of core 14, lip segment 90o is configured to contact the vestibular portions of the user's central incisors thereby forming a positive stop to prevent further insertion of the guard into the user's mouth during the custom fitting process.

FIGS. 45 and 46 illustrate an embodiment of a core 14p that is similar to core 14o, except that lip segment 90p extends slightly past edge 88p in an inferior direction.

FIGS. 47 and 48 illustrate an embodiment of a core 14q that is similar to core 14o except that lip segment 90q has been elongated so as to contact the vestibular portions of the user's lateral incisors as well as the user's central incisors thereby giving a greater surface area for the stop which prevents further insertion of the guard into the user's mouth during the custom fitting process.

FIGS. 49-52 illustrate an embodiment of a core 14r that is similar to core 14e of FIGS. 22 and 23, except that anterior arch segment 14r, and in particular end sections 48r, is configured differently. In particular, the vestibular margin 92 of end sections 48r are curved inwardly, thereby reducing the width of end section 48r relative to end section 48 of core 14. The inward curvature of margin 92 generally coincides with the transition between the user's cuspid and bicuspid teeth. This inward curvature better accommodates the additional cusp present on the lingual side of each bicuspid, particularly if the user's teeth are out of alignment.

Figure 53:
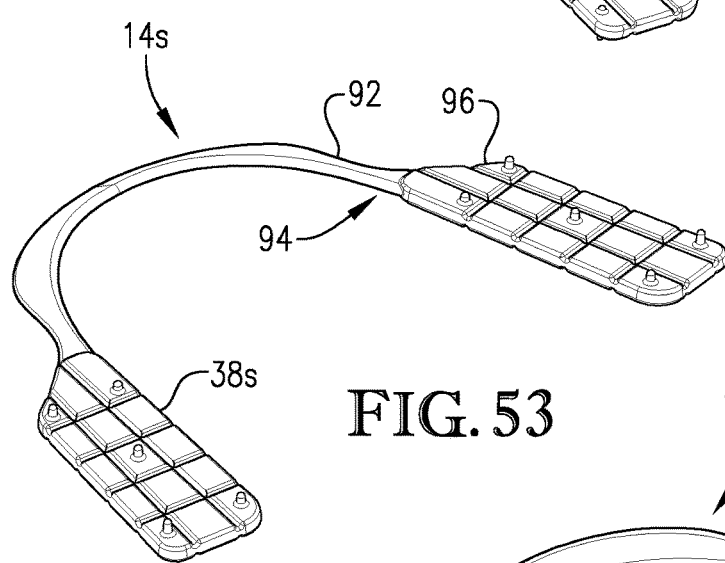
FIG. 53 is a top isometric view of another embodiment of a core that may be utilized in the construction of a dental guard according to the present invention having recessed anterior bite pad portion in addition to the recessed posterior portion of the anterior arch segment.
Figure 54:
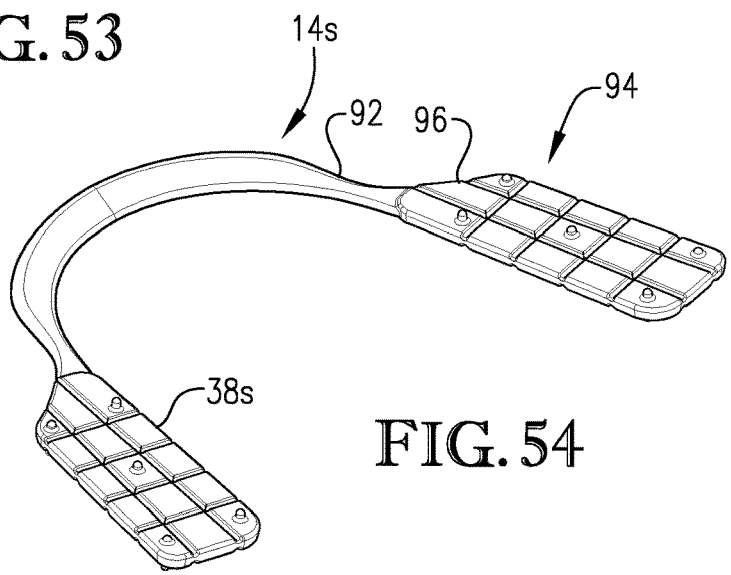
FIG. 54 is a bottom isometric view of the core of FIG. 53.

FIGS. 53 and 54 illustrate an embodiment of a core 14s that is similar to core 14r except that the curvature that begins with vestibular margin 92 continues on to the anterior portion 94 of bite pads 38s. The vestibular margin 96 of the bite pad anterior portion 94 is of a more concave configuration as opposed to convex as with core 14r. Again, this extended curvature better accommodates the additional cusps of the user's bicuspid teeth.

Figure 55:
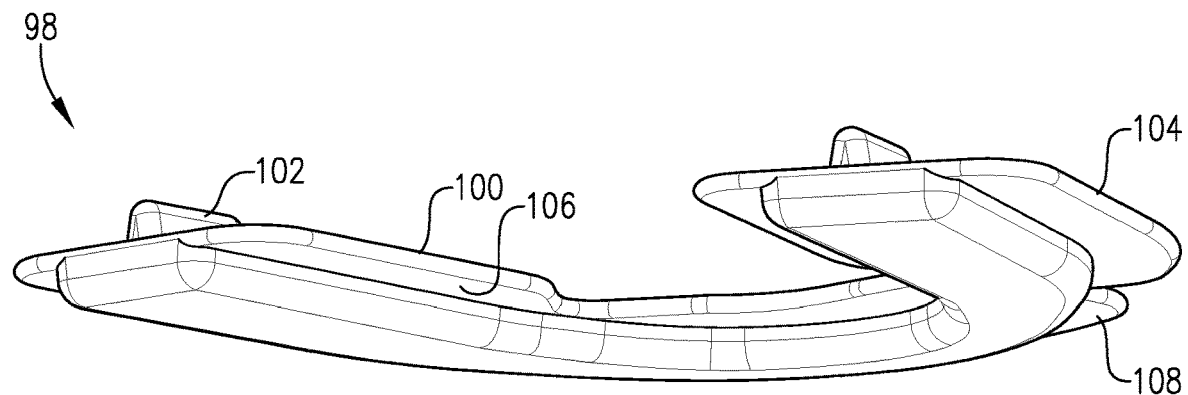
FIG. 55 is a bottom isometric view of another embodiment of a dental guard in accordance with the present invention.
Figure 56:
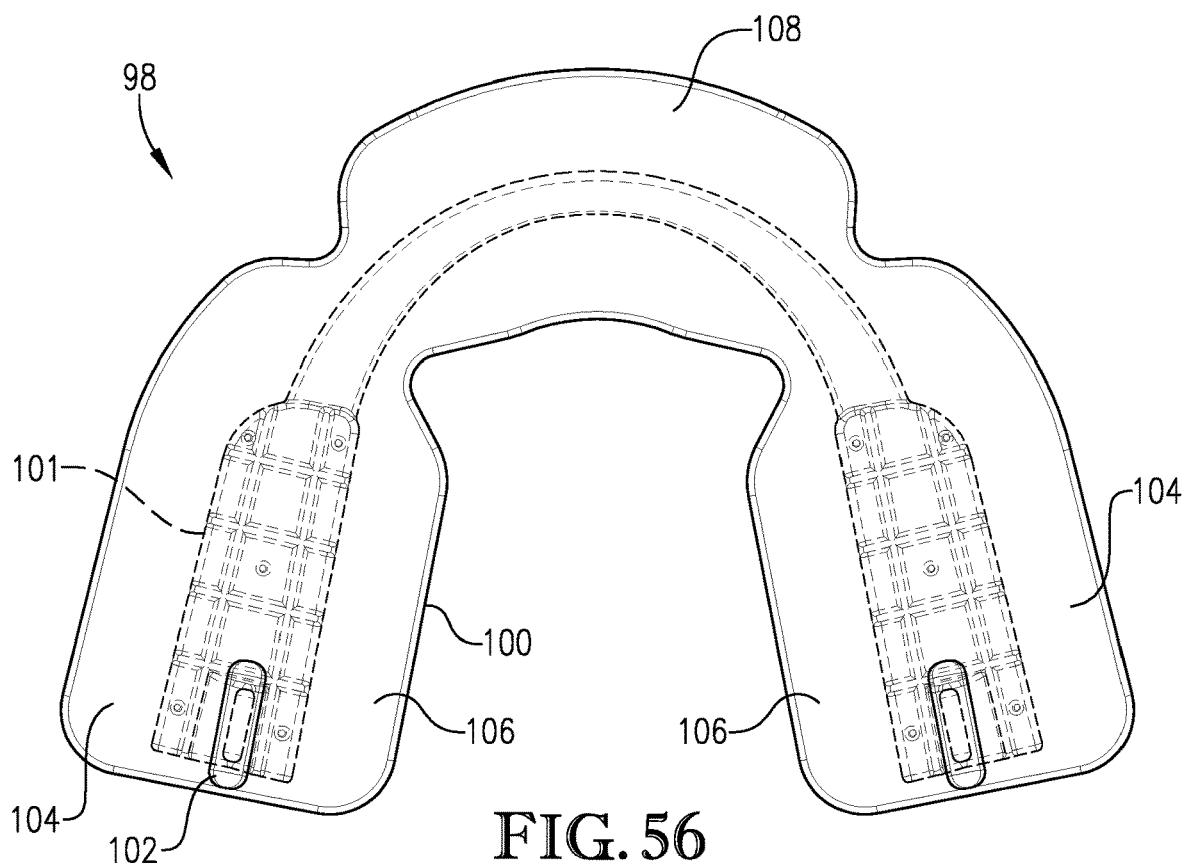
FIG. 56 is a top plan view of the dental guard of FIG. 55.
Figure 57:
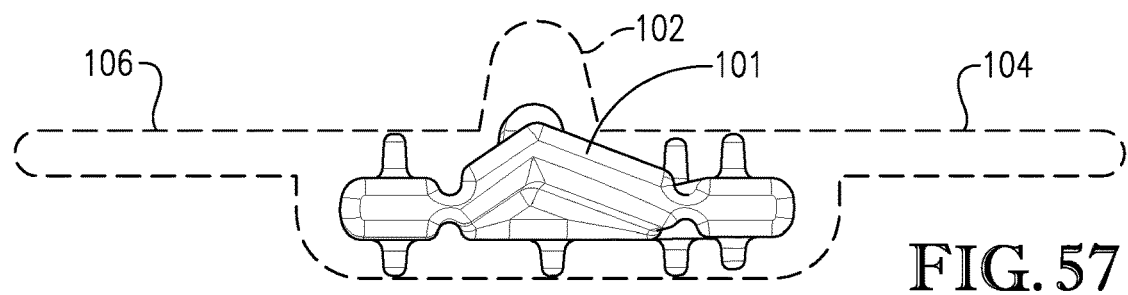
FIG. 57 is a partial end view of the dental guard of FIG. 55 with the outer layer shown in phantom.

FIGS. 55-57 illustrate an embodiment of a dental guard 98 that is not provided with a preformed channel into which the user's maxillary teeth are inserted. Guard 98 comprises an outer layer 100 that is overmolded about a core 101, such as core 14m from FIG. 38, although any core described herein may be used. The outer layer 100 includes positioning elements 102 that are configured as described above. Instead of a preformed channel that is defined by upstanding sidewalls, outer layer 100 comprises moldable buccal 104, lingual 106, and anterior 108 flange sections, that during the custom-fitting process, can be formed around the user's maxillary teeth to provide a clinical-style fit. Alternatively, flanges 104, 106, and 108 can be sized so as to approximate the dimensions of core 101, or only extend only short distance beyond the margins thereof, leaving very little of outer layer 100 to be molded to the buccal, facial, and lingual surfaces of the user's maxillary teeth.

Figure 58:
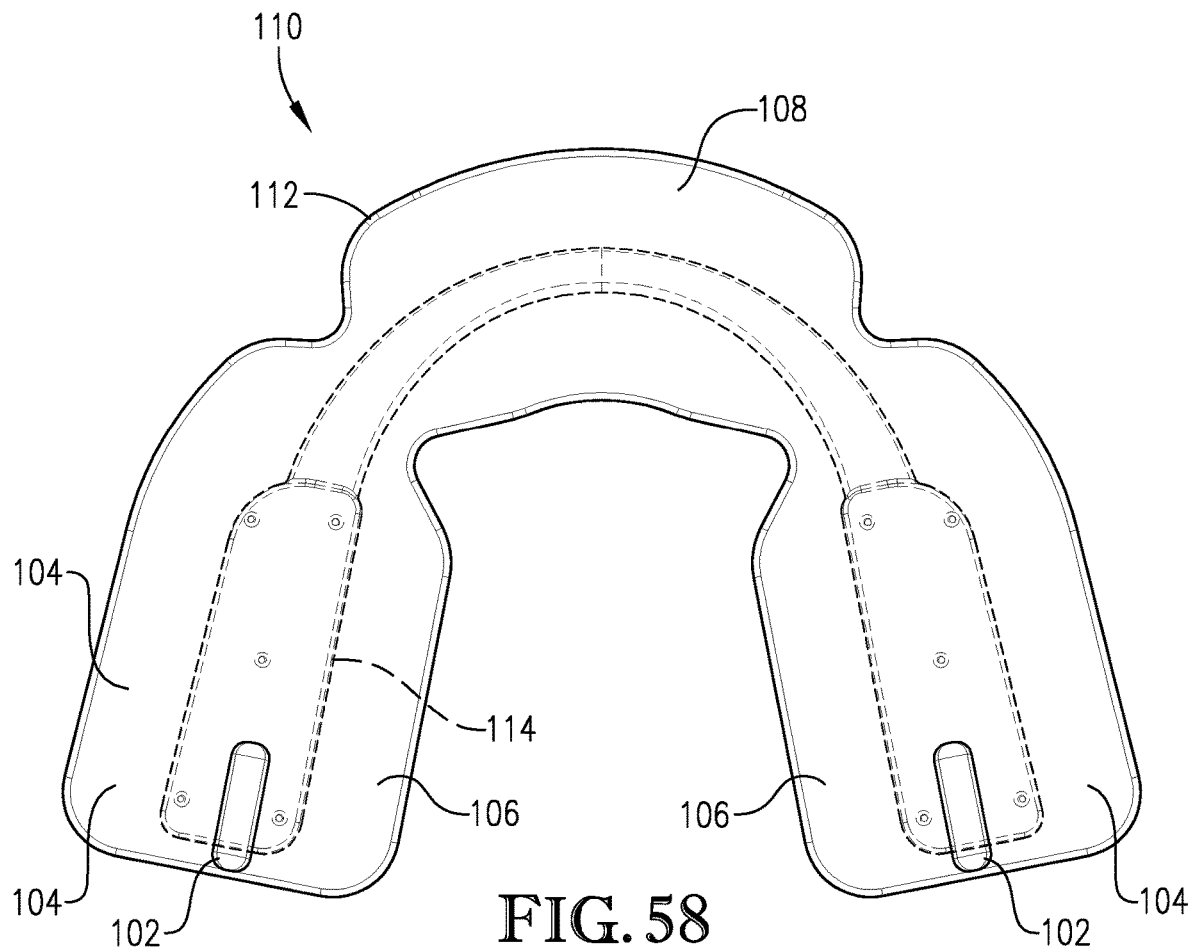
FIG. 58 is a top plan view of another embodiment of a dental guard in accordance with the present invention.
Figure 59:
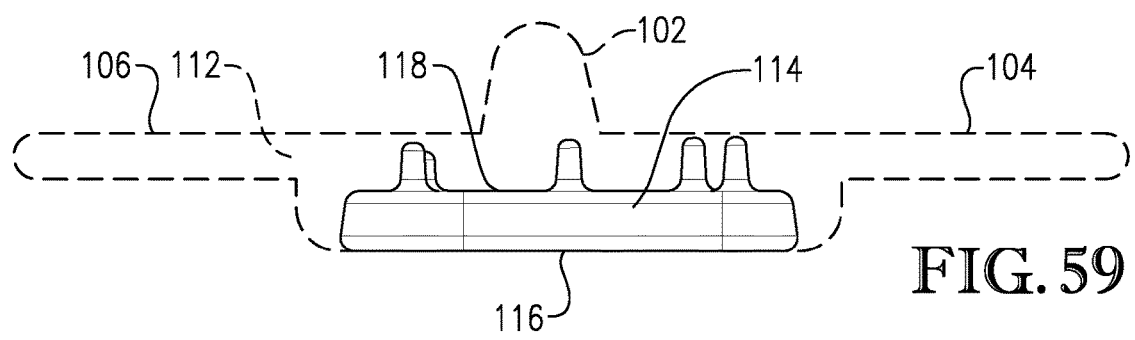
FIG. 59 is a partial end view of the dental guard of FIG. 58 with the outer layer shown in phantom.

FIGS. 58 and 59 illustrate an embodiment of a dental guard 110 that is similar in certain respects to dental guard 98; however, instead of being fully overmolded by outer layer 112, core 114 comprises an exposed mandibular occlusal surface 116. The maxillary occlusal surface 118 of core 114 is overmolded by outer layer 112. It is noted that outer layer 112 may extend upwardly only from maxillary occlusal surface 118, or also overlie core side margins 120, as shown in FIG. 59.

Figure 60:
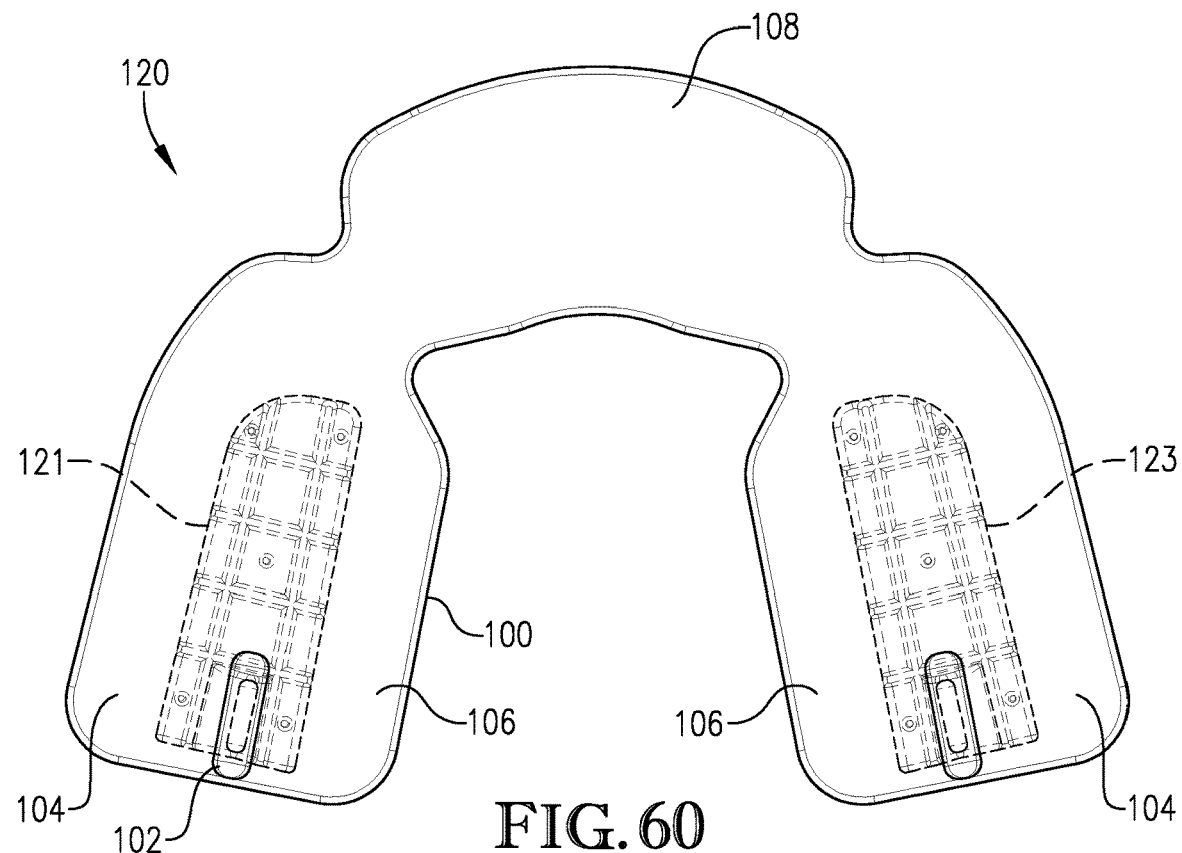
FIG. 60 is a top plan view of another embodiment of a dental guard in accordance with the present invention.

FIG. 60 illustrates an embodiment of a dental guard 120 that is similar in certain respects to dental guard 98 of FIG. 56, except that guard comprises bite pads 121, 123 that are not interconnected by an anterior arch segment. Thus, bite pads 121, 123 are independent of each other and interconnected only by outer layer 100. It is further noted that dental guard 120 is depicted as not having a pre-formed channel, but it is within the scope of the present invention for guard 120 to comprise a pre-formed channel similar to guard 10 of FIG. 3.

Figure 61:
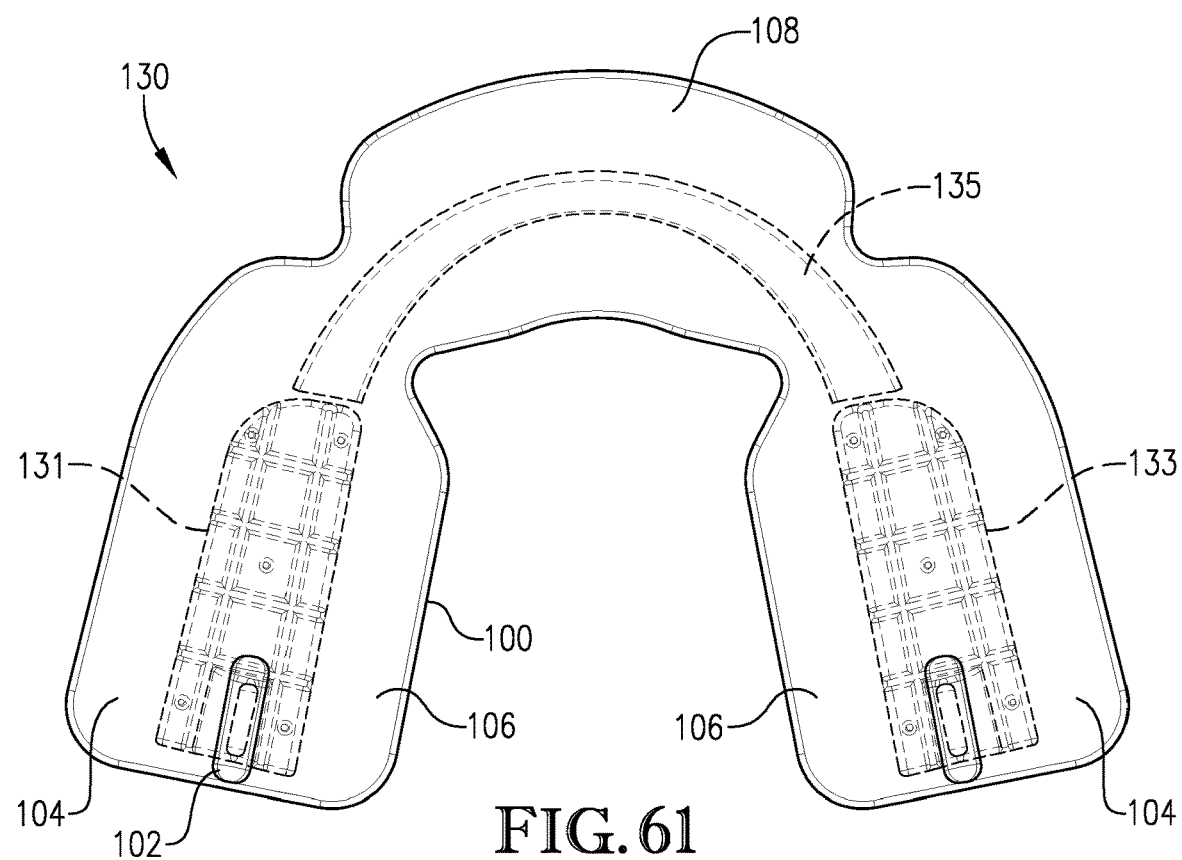
FIG. 61 is a top plan view of still another embodiment of a dental guard in accordance with the present invention.

FIG. 61 illustrates still another embodiment of a dental guard 130 that is similar to dental guard 120 and comprises bite pads 131, 133, and an anterior arch segment 135. Note, anterior arch segment 135 is not directly coupled with either of the bite pads 131, 133. Instead, the anterior arch segment 135 is independent of the bite pads 131, 133 and interconnected therewith via outer layer 100. Thus, guard 130 comprises a core structure made up of three independent parts. Like guard 120, guard 130 may also comprise a pre-formed channel similar to guard 10 of FIG. 3.

Figure 62:
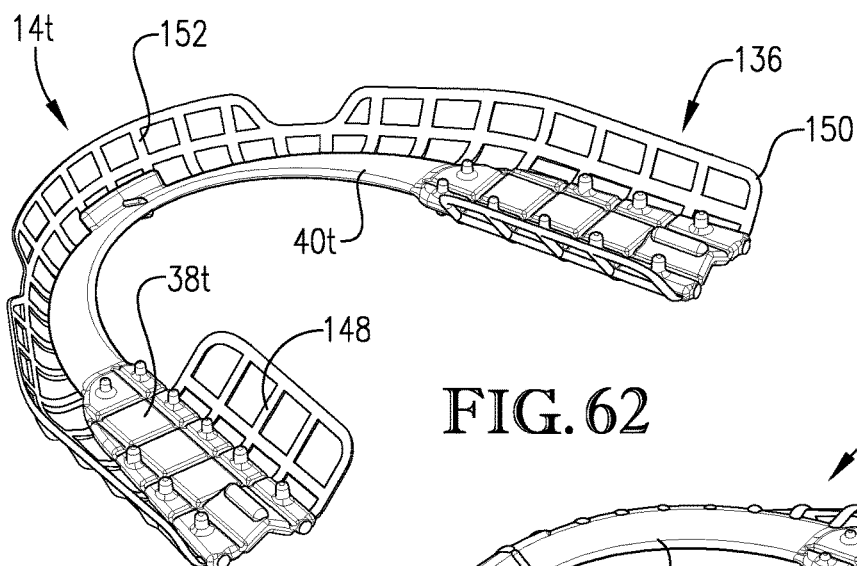
FIG. 62 is a top isometric view of another embodiment of a core that may be utilized in the construction of a dental guard according to the present invention having grid-like frame structure extending from the bite pads and arch segment.
Figure 63:
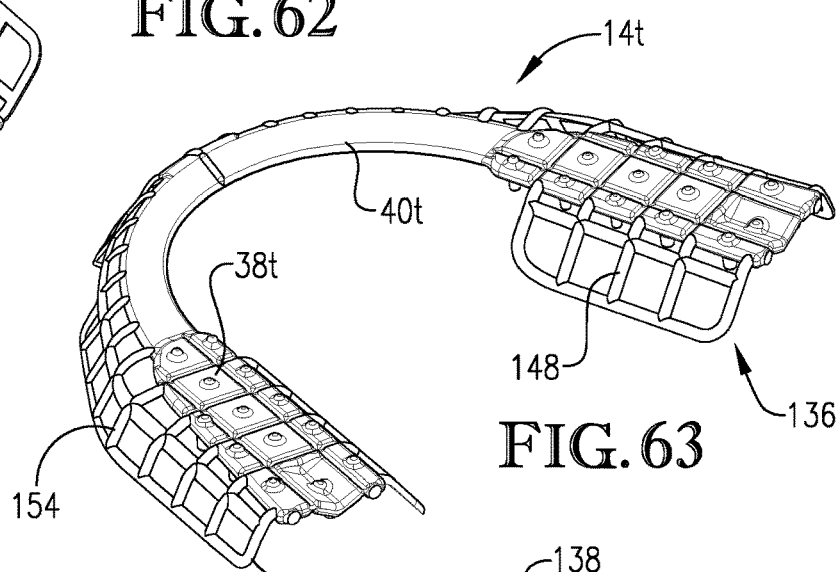
FIG. 63 is a bottom isometric view of the core of FIG. 62.
Figure 64:
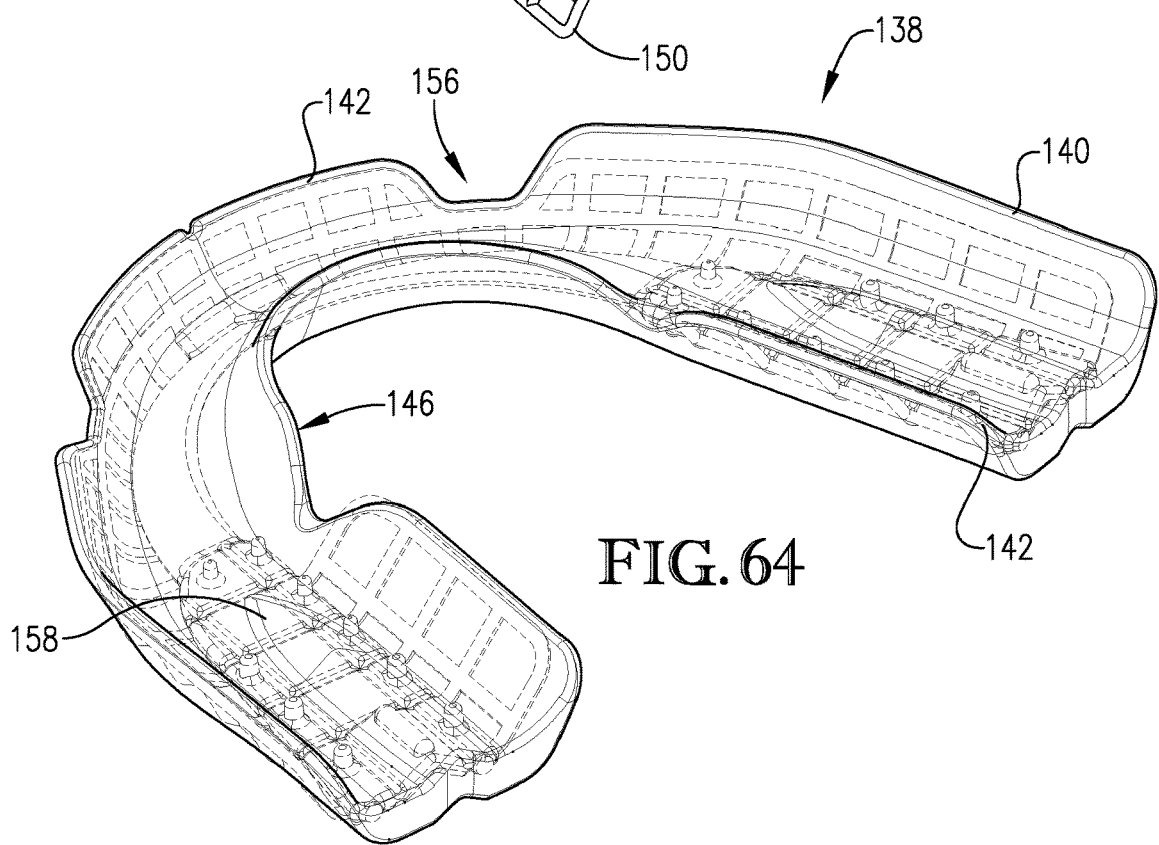
FIG. 64 is a top isometric view of a dental guard comprising the core of FIG. 62.

FIGS. 62 and 63 illustrate an embodiment of a core 14t that comprises bite pads 38t interconnected by arch segment 40t. In many respects, core 14t comprises a number of the same or similar features as core 14 from FIGS. 8-10. In addition, core 14t comprises a lattice structure 136 that is coupled with bite pads 38t and arch segment 40t. When core 14t is incorporated into a dental guard 138, as illustrated in FIG. 64, the lattice structure 136 is operable to support buccal sidewalls 140, lingual sidewalls 142, and facial sidewall 144. In particular, when, during the fitting process, outer layer 146 is softened and then conformed to the wearer's teeth, lattice structure 136 provides structural integrity to the surrounding outer layer 146 so as to avoid collapse of the various sidewalls and assist the user in being able to achieve a comfortable fit. In addition, lattice structure 136 creates a constraint against shrinkage of the outer layer 146 post-fitting.

In certain embodiments, lattice structure 136 is formed from the same material as the other portions of core 14t. However, lattice structure 136 is generally much thinner than the other portions of the core, in some embodiments approximately 0.010-0.030 inch, or preferably 0.020 inch, so that it presents a greater level of flexibility than the rest of the core. Lattice 136 comprises a network of interconnected, generally rectilinear segments 148 and/or curvilinear segments 150 that are unitary and not independent from each other. In certain embodiments, the lattice structure 136 is formed simultaneously with the other portions of core 14t during, for example, an injection molding process. At least one of segments 148 or 150 are attached to or otherwise extend away from bite pad 38t. In addition, at least one of segments 148 or 150 extend transversely from the bite pad 38t in a direction that is generally outboard of the bite pad and toward the maxilla of the user. Others of segments 148 or 150 may extend transversely from other segments in order to provide structural integrity to the lattice and mild resistance to relative movement of the segments relative to each other. In particular embodiments, some of segments 148 or 150 are oriented generally parallel to a plane in which at least a portion of the bite pad 38t resides, and some of segments 148 or 150 are oriented generally transverse to said plane. To assist with manufacturing, the lingual side 152 of segments 148, 150 may be flat, while the buccal or facial side 154 of lattice structure 136 may curved or rounded, or vice versa. This configuration has the further benefit of enhancing the flexural characteristics of the lattice 136 during the fitting process. It is understood that lattice structure 136 need not comprise all segments 148 and 150 that are illustrated in FIGS. 62-64. It is also within the scope of the present invention for certain ones of segments 148 and 150 to extend only from the bite pads 38t or arch segment 40t and not be connected with any other individual, transversely-extending segments, giving those segments a tine-like configuration. Thus, the interconnectedness of those segments would be by way of the bite pads and/or arch segment.

In the embodiment of dental guard 138 illustrated in FIG. 64, it is noted that the labial recesses 156 have been slightly narrowed as compared with other embodiments. In addition, positioning elements 158, formed from the overmolded outer layer 146 have been enlarged and given a dart or bullet-like shape to further assist in guiding these elements into and filling the occlusal groove of the user's molars during the fitting process.

Figure 65:
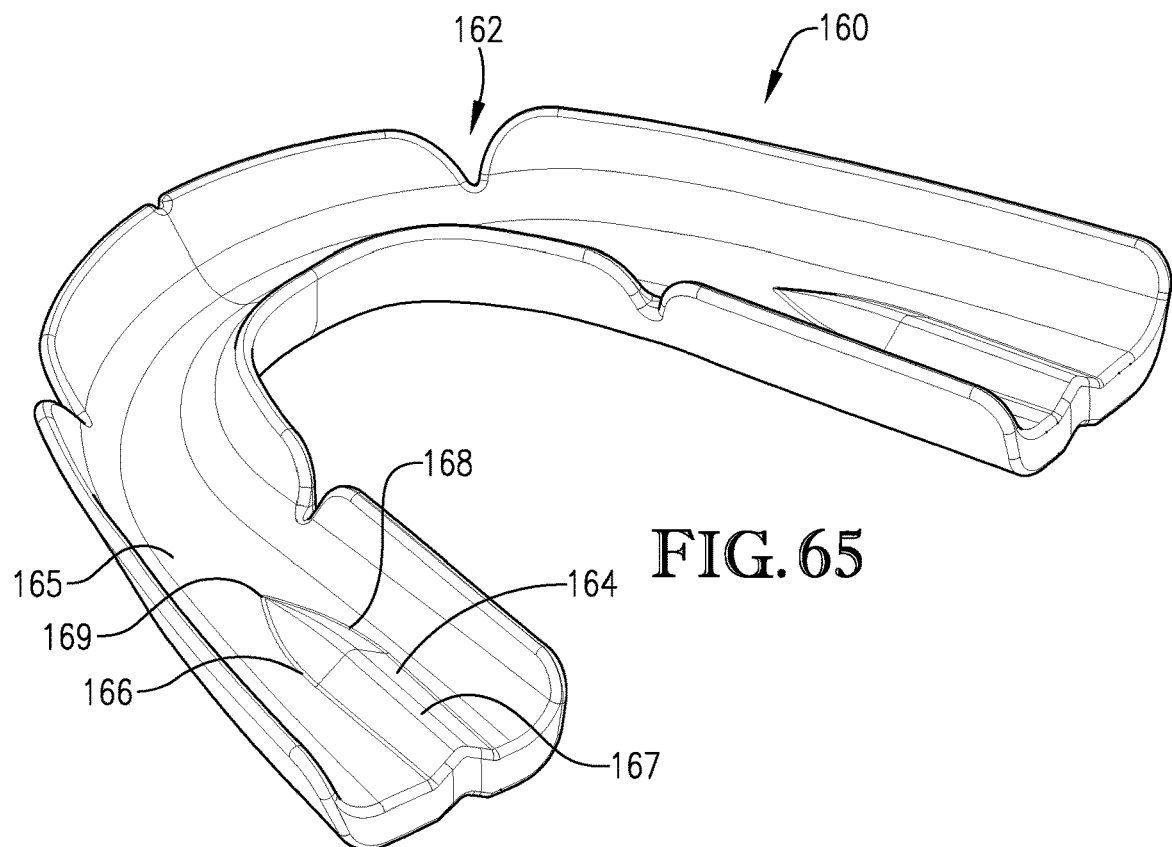
FIG. 65 is a top isometric view of a dental guard according to the present invention.
Figure 66:
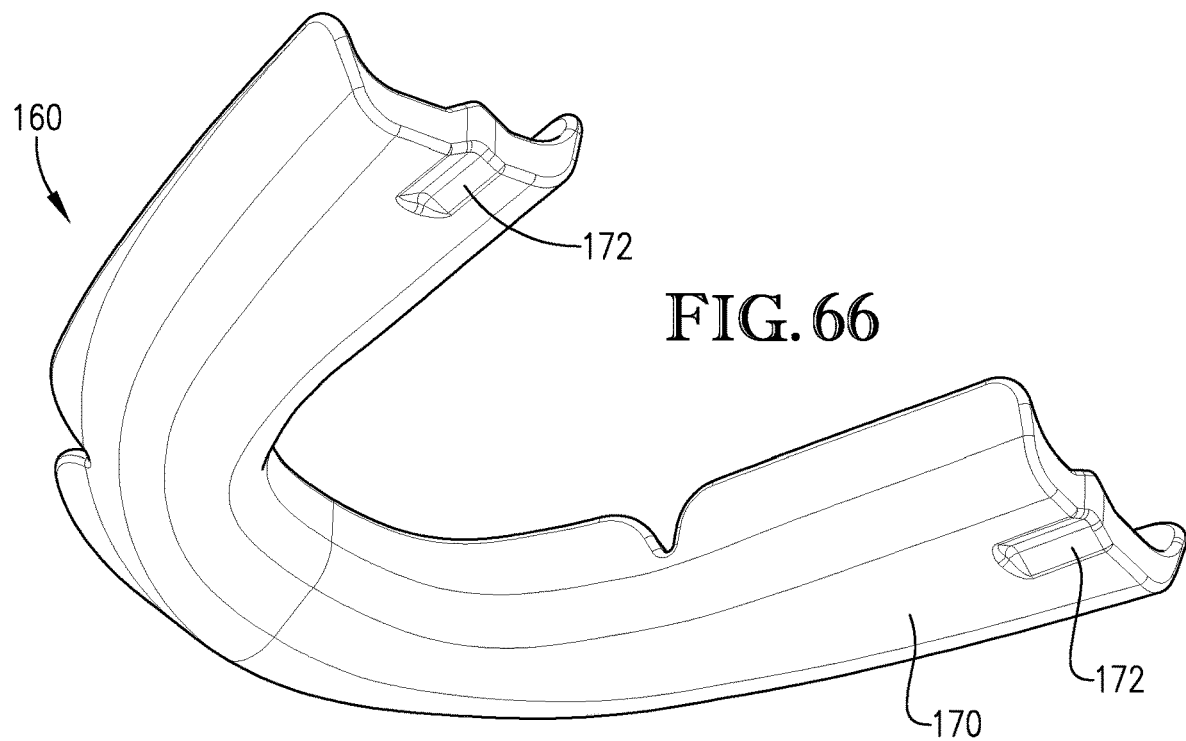
FIG. 66 is a bottom isometric view of the dental guard of FIG. 65.

FIGS. 65 and 66 illustrate another embodiment of a dental guard 160 made in accordance with the present invention. This embodiment is very similar to that which is illustrated in FIG. 63, except that labial recesses 162 have been further narrowed. Dental guard 160 may comprise a core having the lattice structure 136 of FIGS. 62 and 63, or any other type of core disclosed herein, or no core at all. Positioning elements 164 are generally configured with margins 166, 168 that converge in the anterior direction of the guard 160 and terminate at a tip 169. Positioning elements 164 further comprise a central ridge 167 that extends the length of the element and slopes downwardly toward the maxillary occlusal surface 165 toward tip 169. In addition, as best shown in FIG. 66, the mandibular occlusal surface 170 of bite guard 160 comprises a notch 172 formed opposite positioning elements 164. In certain embodiments, notch 172 may correspond with the mandibular occlusal side of peaked segment 72 from, for example, core 14 of FIGS. 8 and 9.

I claim:

1. A method of manufacturing a dental guard comprising: overmolding a core formed from a first material having a first softening point temperature with a second material having a second softening point temperature using an injection molding process, the core comprising a pair of bite pads interconnected by an anterior arch segment, each of the bite pads comprising opposed maxillary and mandibular occlusal surfaces, the second material forming an outer layer that substantially covers the maxillary and mandibular occlusal surfaces of the bite pads and defines, at least in part, a maxillary surface adapted to contact maxillary teeth of a user, the second softening point temperature being less than the first softening point temperature, wherein the bite pads comprise a positioning element located in a posterior portion of each bite pad and extending from the maxillary occlusal surface of each bite pad, the positioning element being adapted to be received in the occlusal groove between the buccal and lingual cusps of a maxillary molar, wherein the positioning element is located on a peaked segment of the bite pad posterior portion, the peaked segment being formed by intersecting sloped bite pad segments.

2. The method of claim 1, wherein the positioning element comprises a rib having a length that runs longitudinally with respect to the bite pad.

3. The method of claim 1, the second softening point temperature being at least 20° C. lower than the first softening point temperature.

4. The method of claim 1, wherein the second softening point temperature is less than 90 C.

5. The method of claim 1, wherein the second softening point temperature is from about 40° C. to about 80° C.

6. The method of claim 1, wherein the first softening point temperature is greater than 80° C.

7. The method of claim 1, wherein the portion of the outer layer that substantially covers the maxillary occlusal surface is thicker than the portion of the outer layer that substantially covers the mandibular occlusal surface.

8. The method of claim 1, wherein the core comprises a lattice structure that extends from the bite pads and the anterior arch segment.

9. The method of claim 1, wherein the first material comprises a polyurethane, polycaprolactone, polypropylene, polyester, or methacrylate resin material, and wherein the core is formed using an injection molding process.

10. The method of claim 1, wherein the second material comprises polycaprolactone.

11. The method of claim 1, wherein each of the bite pads has a thickness that is greater than the thickness of at least a portion of the anterior arch segment.

12. The method of claim 1, the pair of bite pads each comprising at least one offset extending from the maxillary occlusal surface and at least one offset extending from the mandibular occlusal surface.

13. The method of claim 12, wherein the offset extending from the maxillary occlusal surface is longer than the offset extending from the mandibular occlusal surface.

14. The method of claim 1, wherein each of the bite pads comprise one or more hinges formed therein that divide the bite pads into respective bite pad segments, the one or more hinges permitting pivoting of at least one bite pad segment relative to another bite pad segment.

15. The method of claim 14, each of the bite pads comprising at least two hinges, wherein at least one hinge in each bite pad is parallel to a longitudinal axis of the bite pad and at least one other hinge in each bite pad is transverse to the longitudinal axis of the bite pad.

16. The method of claim 14, wherein the one or more hinges comprise an area of reduced thickness in the bite pads.

17. The method of claim 16, wherein the area of reduced thickness in the bite pads comprises a pair of superposed trenches, one of the trenches being formed in the maxillary occlusal surface and the other of the trenches being formed in the mandibular occlusal surface.

\* \* \* \* \*